(12) United States Patent
Camber et al.

(10) Patent No.: US 12,121,614 B2
(45) Date of Patent: Oct. 22, 2024

(54) DELAYED RELEASE COMPOSITION FOR PERORAL ADMINISTRATION

(71) Applicant: VICORE PHARMA AB, Stockholm (SE)

(72) Inventors: Ola Camber, Stockholm (SE); Christina Johansson, Gothenburg (SE)

(73) Assignee: VICORE PHARMA AB, Stockholm (SE)

( * ) Notice: Subject to any disclaimer, the term of this patent is extended or adjusted under 35 U.S.C. 154(b) by 0 days.

(21) Appl. No.: 18/300,739

(22) Filed: Apr. 14, 2023

(65) Prior Publication Data

US 2023/0364022 A1   Nov. 16, 2023

Related U.S. Application Data

(63) Continuation of application No. 17/696,997, filed on Mar. 17, 2022, now Pat. No. 11,654,115, which is a continuation of application No. PCT/GB2021/050993, filed on Apr. 23, 2021.

(30) Foreign Application Priority Data

Apr. 24, 2020   (GB) .................................... 2006074

(51) Int. Cl.
*A61K 9/28* (2006.01)
*A61K 9/00* (2006.01)
*A61K 9/48* (2006.01)
*A61K 31/4178* (2006.01)

(52) U.S. Cl.
CPC .......... *A61K 9/4866* (2013.01); *A61K 9/0056* (2013.01); *A61K 9/4808* (2013.01); *A61K 9/4825* (2013.01); *A61K 31/4178* (2013.01)

(58) Field of Classification Search
CPC ...... A61K 9/48; A61K 9/4808; A61K 9/4816; A61K 9/4841; A61K 9/485; A61K 9/4891; A61K 9/4866
See application file for complete search history.

(56) References Cited

U.S. PATENT DOCUMENTS

| | | | |
|---|---|---|---|
| 10,154,990 B2 | 12/2018 | Park et al. | |
| 11,654,115 B2 | 5/2023 | Camber et al. | |
| 11,819,494 B2 | 11/2023 | Dalsgaard et al. | |
| 11,844,868 B2 | 12/2023 | Camber et al. | |
| 2005/0143435 A1 | 6/2005 | Baum et al. | |
| 2019/0000768 A1 | 1/2019 | Shimokawa et al. | |

FOREIGN PATENT DOCUMENTS

| | | | | |
|---|---|---|---|---|
| JP | S59139317 | A | 8/1984 | |
| JP | 2003325642 | A | 11/2003 | |
| JP | 2019182746 | A | 10/2019 | |
| WO | 99/43339 | A1 | 9/1999 | |
| WO | 2002/096883 | A1 | 12/2002 | |
| WO | WO-2005123072 | A1 * | 12/2005 | ........... A61K 31/135 |
| WO | 2015177025 | A1 | 11/2015 | |
| WO | 2015177028 | A1 | 11/2015 | |
| WO | WO-2016139475 | A1 * | 9/2016 | ........... A61K 31/401 |
| WO | 2017022248 | A1 | 2/2017 | |
| WO | 2017/221012 | A1 | 12/2017 | |
| WO | 2019/008393 | A1 | 1/2019 | |
| WO | 2019/183513 | A1 | 9/2019 | |
| WO | 2020/095042 | A1 | 5/2020 | |

OTHER PUBLICATIONS

Maderuelo et al (https://doi.org/10.1016/j.ejps.2019.105019) (Year: 2019).*
Crowley et al (Immunologic Effects of the Renin-Angiotensin System, J Am Soc Nephrol 28: 1350-1361, 2017) (Year: 2017).*
Guidance for Industry, "Food-Effect Bioavailability and Fed Bioequivalence Studies," U.S. Department of Health and Human Services, Food and Drug Administration, Center for Drug Evaluation and Research (CDER) Dec. 2002.
Decision of Rejection for Japan Application No. 2022-540547, mailed May 30, 2023 (English Translation).
O.R.L. Tokyo 45(4):292-295 (2002) (with English Translation).
J. Okayama Med. Assoc. 127:245-249 (2015) (with English Translation).
Drug Delivery System 25(4):384-391 (2010) (with English Translation).
Office Action in U.S. Appl. No. 17/696,997 mailed Jul. 8, 2022.
Office Action in U.S. Appl. No. 17/696,997, mailed Nov. 22, 2022.
Lawrence and Bing, "FDA Bioequivalence Standards" AAPS Advances in the Pharmaceutical Sciences Series 13. Springer New York Heidelberg Dordrecht London.
Lee et al., "The Effect of Food and Tablet Formulation on Plasma Prednisolone Levels Following Administration of Enteric-coated Tablets," Br. J. Clin. Pharmacol. 7:523-528 (1979).
Rathinasabapathy et al., "The Selective Angiotensin II Type 2 Receptor Agonist, Compound 21, Attenuates the Progression of Lung Fibrosis and Pulmonary Hypertension in an Experimental Model of Bleomycin-Induced Lung Injury," Front. Physiol. 9, Article 180 (2018).
Hashmat et al., "Developmeni of Enteric Coated Flurbiprofen Tablets using Opadryiacryl-eze System—A Technical Note," AAPS PharmSciTech. 9(1):116-121 (2008).
King et al., "Idiopathic Pulmonary Fbrosis," Lancet 378:1949-1961 (2011).

(Continued)

*Primary Examiner* — Micah Paul Young
(74) *Attorney, Agent, or Firm* — Troutman Pepper Hamilton Sanders LLP (Rochester)

(57) ABSTRACT

According to the invention there is provided a pharmaceutical composition comprising N-butyloxycarbonyl-3-(4-imidazol-1-ylmethylphenyl)-5-iso-butylthiophene-2-sulfonamide (C21), or a pharmaceutically-acceptable salt thereof, in which composition the C21 or salt thereof is protected by the presence of a coating comprising an enteric substance. Preferred dosage forms comprise capsules in which C21 or salt thereof is presented in the form of a dry powder mixture or a suspension of particles of C21 in a solvent in which it is insoluble. Such dosage forms find utility in the treatment of lung diseases, such as idiopathic pulmonary fibrosis, sarcoidosis and respiratory virus-induced tissue damage.

16 Claims, No Drawings

(56) References Cited

OTHER PUBLICATIONS

Noble et al., "Pulmonary Fibrosis: Patterns and Perpetrators," J. Clin. Invest. 122:2756-2762 (2012).
Ley et al., "Clinical Course and Prediction of Survival in IdiopathicPulmonary Fibrosis," Am. J. Respir. Crit. Care Med. 183:431-440 (2011).
Rafii et al., "A Review of Current and Novel Therapies for Idiopathic Pulmonary Fibrosis," J. Thorac. Dis. 5:48-73 (2013).
De Gasparo et al., "International Union of Pharmacology. XXIII. The Angiotensin II Receptors," Pharmacol. Rev. 52:415-472 (2000).
Lawrence and Bing, "FDA Bioequivalence Standards" AAPS Advances in the Pharmaceutical Sciences Series 13. Springer New York Heidelberg Dordrecht London, Dec. 2002.
International Preliminary Report on Patentability for PCT/GB2021/050993, dated Mar. 28, 2022.
Crowley et al., "Immunologic Effects of the Renin-Angiotensin System," J Am Soc Nephrol 28:1350-1361 (2017).
Steckelings et al., "Correcting the Imbalanced Protective RAS in COVID-19 With Angiotensin AT2-Receptor Agonists," Clinical Science 134:2987-3006 (2020).

\* cited by examiner

DELAYED RELEASE COMPOSITION FOR PERORAL ADMINISTRATION

This application is a continuation of U.S. patent application Ser. No. 17/696,997, filed Mar. 17, 2022, which is a continuation of PCT/GB2021/050993, filed Apr. 23, 2021, which is hereby incorporated by reference in its entirety, and which claims priority benefit of GB 2006074.5, filed Apr. 24, 2020.

FIELD OF THE INVENTION

This invention relates to new pharmaceutical dosage forms, their use as medicaments and particularly to their administration to treat, inter alia, lung diseases, for example interstitial lung diseases.

Background and Prior Art

Interstitial lung diseases (ILDs) are a group of lung diseases that affect the interstitium, characterized by tissue around alveoli becoming scarred and/or thickened, and so inhibiting the respiratory process.

ILDs are distinct from obstructive airway diseases (e.g. chronic obstructive airway disease (COPD) and asthma), which are typically characterized by narrowing (obstruction) of bronchi and/or bronchioles. ILDs may be caused by injury to the lungs, which triggers an abnormal healing response but, in some cases, these diseases have no known cause. ILDs can be triggered by chemicals (silicosis, asbestosis, certain drugs), infection (e.g. pneumonia) or other diseases (e.g. rheumatoid arthritis, systemic sclerosis, myositis, hypersensitivity pneumonitis or systemic lupus erythematosus).

The most common ILDs are idiopathic pulmonary fibrosis (IPF) and sarcoidosis, both of which are characterized by chronic inflammation and reduced lung function.

Sarcoidosis is a disease of unknown cause that is characterized by collections of inflammatory cells that form lumps (granulomas), often beginning in the lungs (as well as the skin and/or lymph nodes, although any organ can be affected). When sarcoidosis affects the lungs, symptoms include coughing, wheezing, shortness of breath, and/or chest pain.

Treatments for sarcoidosis are patient-specific. In most cases, symptomatic treatment with non-steroidal anti-inflammatory drugs (NSAIDs) is possible, but for those presenting lung symptoms, glucocorticoids (e.g. prednisone or prednisolone), antimetabolites and/or monoclonal anti-tumor necrosis factor antibodies are often employed.

IPF is a lung-disease of unknown cause that affects about 5 million people globally. It has no curative treatment options except, in rare cases, lung transplantation, resulting in a chronic, irreversible, progressive deterioration in lung function and, in most cases, leading to death within 2-5 years (median survival 2.5 to 3.5 years). While the overall prognosis is poor in IPF, it is difficult to predict the rate of progression in individual patients. Risk factors for IPF include age, male gender, genetic predisposition and history of cigarette smoking. The annual incidence is between 5-16 per 100,000 individuals, with a prevalence of 13-20 cases per 100,000 people, increasing dramatically with age (King Jr T E et al., Lancet (2011) 378, 1949-1961; Noble P W et al., J. Clin. Invest. (2012) 122, 2756-2762). IPF is limited to the lungs and is recalcitrant to therapies that target the immune system which distinguishes it from pulmonary fibrosis (PF) associated with systemic diseases.

Patients with IPF usually seek medical assistance due to chronic and progressive exertional dyspnea and cough. Imaging of the lung classically reveals traction bronchiectasis, thickened interlobar septae and subpleural honeycombing. When all three manifestations are present and there is no evidence of a systemic connective tissue disease or environmental exposure, a diagnosis of IPF is very likely. A definite diagnosis is usually made by lung biopsy and requires a multidisciplinary team of expertise including pulmonologists, radiologists and pathologists experienced in ILDs.

IPF demonstrates different phenotypes with different prognosis, defined as mild, moderate and severe. Mild cases follow a stable or slow progressive path with patients sometimes taking several years to seek medical advice. Accelerated IPF has a much more rapid progression with shortened survival, affecting a sub-group of patients, usually male cigarette smokers. Acute exacerbations of IPF are defined as a rapid worsening of the disease, and patients in this sub-population have very poor outcomes with a high mortality rate in the short run. The cause of IPF is unknown but it appears to be a disorder likely arising from an interplay of environmental and genetic factors resulting in fibroblast driven unrelenting tissue remodeling rather than normal repair; a pathogenesis primarily driven by fibrosis rather than inflammation. A growing body of evidence suggests that the disease is initiated through alveolar epithelial cell microinjuries and apoptosis, activating neighboring epithelial cells and attracting stem or progenitor cells that produce the factors responsible for the expansion of the fibroblast and myofibroblast populations in a tumor like way. The fibroblastic foci secrete exaggerated amounts of extracellular matrix that destroys the lung parenchyma and ultimately leads to loss of lung function.

The mean annual rate of decline in lung function (vital capacity) is within a range of 0.13-0.21 litres. Symptoms precede diagnosis by 1-2 years and radiographic signs may precede symptoms (Ley B et al., Am. J. Respir. Crit. Care Med. (2011) 183, 431-440).

Numerous treatment approaches have been tested in preclinical models and clinical trials such as anti-inflammatory, immune-modulatory, cytotoxic, general anti-fibrotic, anti-oxidant, anti-coagulant, anti-chemokine, anti-angiogenic drugs as well as RAS-blockers, endothelin antagonists, and sildenafil, all of which have basically been shown to provide limited or no benefits (Rafii R et al., J. Thorac. Dis. (2013) 5, 48-73).

Current treatment of IPF includes oxygen supplementation. Medications that are used include pirfenidone or nintedanib, but only with limited success in slowing the progression of the disease. Further, both of these drugs commonly cause (predominantly gastrointestinal) side-effects.

There are drawbacks associated with all of the aforementioned ILD (and IPF) drug treatments and there is a real clinical need for safer and/or more effective treatments.

To restore the alveolar epithelium is very desirable as a therapeutic effect in IPF, and therefore stem cell therapy has also been tested. Some preclinical studies have shown promise in the use of pluripotent stem cells that can differentiate into lung epithelial and endothelial cells, thereby repairing lung injury and fibrosis.

Currently, a lung transplant is the only intervention that substantially improves survival in IPF patients. However, complications such as infections and transplant rejection are not uncommon.

The development of new treatment strategies for IPF is therefore important. Thus, the fundamental challenge for the future is to develop appropriate therapeutic approaches that will reverse or stop the progression of the disease.

The Renin-Angiotensin System (RAS) is a key regulator of blood pressure homeostasis. Renin, a protease, cleaves its only known substrate (angiotensinogen) to form angiotensin I (Ang I), which in turn serves as substrate to angiotensin converting enzyme (ACE) to form Ang II. The endogenous hormone Ang II is a linear octapeptide ($Asp^1$-$Arg^2$-$Val^3$-$Tyr^4$-$Ile^5$-$His^6$-$Pro^7$-$Phe^8$), and is an active component of the renin angiotensin system (RAS).

The angiotensin II type 1 (AT1) receptor is expressed in most organs, and is believed to be responsible for the majority of the pathological effects of Ang II. The safety and efficacy of losartan (an AT1-receptor inhibitor) has recently been investigated in a small uncontrolled open-label pilot trial on IPF (www.clinicaltrials.gov identifier NCT00879879).

Several studies in adult individuals appear to demonstrate that, in the modulation of the response following Ang II stimulation, activation of the angiotensin II type 1 (AT2) receptor has opposing effects to those mediated by the AT1 receptor.

The AT2 receptor has also been shown to be involved in apoptosis and inhibition of cell proliferation (de Gasparo M et al., *Pharmacol. Rev.,* 2000; 52:415-472).

AT2 receptor agonists have also been shown to be of potential utility in the treatment and/or prophylaxis of disorders of the alimentary tract, such as dyspepsia and irritable bowel syndrome, as well as multiple organ failure (see international patent application WO 99/43339).

The expected pharmacological effects of agonism of the AT2 receptor are described in general in de Gasparo M et al., supra. It is not mentioned that agonism of the AT2 receptor may be used to treat IPF.

International patent application WO 2002/096883 describes the preparation of imidazolyl, triazolyl, and tetrazolyl thiophene sulfonamides and derivatives as AT2 receptor agonists. Of the compounds described in that document (as Example 1) is N-butyloxycarbonyl-3-(4-imidazol-1-yl-methylphenyl)-5-iso-butylthiophene-2-sulfonamide (Compound 21 or, as used hereinafter 'C21'), which was selected for clinical development from a group of about 20 related analogues as a selective AT2 receptor agonist. C21 is now in clinical development for treatment of disorders in which treatment with an AT2 receptor agonist is believed to be beneficial, including IPF (see, for example, international patent application WO 2016/139475).

Formulative work carried out in respect of C21 and salts thereof has proven extremely difficult. As a consequence, C21 has previously been formulated as an aqueous solution, which is frozen whilst stored and then thawed immediately prior to peroral dosing.

The applicant has been working with this active ingredient for nearly years, and, until recently, has not managed to obtain a pharmaceutically-acceptable dosage form, that is one in which the active ingredient is stable when stored at ambient temperatures.

In addition to this, in a Phase I clinical trial conducted in healthy subjects conducted to evaluate the safety, tolerability, and pharmacokinetics of C21, a pronounced food effect was observed.

This was unexpected, given that the given that unpublished preclinical work in simulated intestinal fluid in both fasted and fed states appeared to be sufficient to allow availability of active ingredient in the gut for good absorption at clinical doses.

Disclosure of the Invention

According to a first aspect of the invention, there is provided a pharmaceutical dosage form that is suitable for peroral administration to the gastrointestinal tract, which dosage form comprises a pharmaceutical composition comprising C21, or a pharmaceutically-acceptable salt thereof, in which composition the C21 or salt thereof is protected by the presence of a coating comprising an enteric substance. Such dosage forms are hereinafter referred to together as 'the dosage forms of the invention'.

Dosage forms of the invention are suitable for peroral administration and delivery, as a complete dosage form, to the gastrointestinal tract. This means that a dosage form of the invention should be suitable for swallowing as a whole, complete dosage form for subsequent consumption and/or ingestion within the gastrointestinal tract, and, in use, is swallowed and then consumed and/or ingested within that tract.

In the context of the present invention, an 'enteric' substance is employed to coat, surround and/or encapsulate a composition comprising C21 or a pharmaceutically-acceptable salt thereof, in order to substantially prevent the active ingredient from being released from that composition within the stomach, and/or coming into contact with gastric juices, and/or until that component reaches the small intestine. By 'substantially preventing', we include that no more than about 20%, such as about 15%, for example about 10%, or more particularly no more than about 5%, of the active ingredient is released within the acidic environment of the stomach.

Typical enteric coating materials include the following: cellulose acetate, cellulose acetate succinate, cellulose acetate phthalate, cellulose acetate tetrahydrophthalate, polyvinyl acetate phthalate, hydroxyethyl ethyl cellulose phthalate, methacrylic acid copolymers, polymethacrylic acid/acrylic acid copolymers, styrol maleic acid copolymers, hydroxypropyl methyl cellulose phthalate, acrylic resins, cellulose acetate trimellitate, hydroxypropyl methylcellulose trimellitate, shellac, hydroxyethyl ethyl cellulose phthalate, carboxymethylcellulose and hydroxypropyl methyl cellulose acetate succinate. Preferred enteric substances include polyvinyl acetate phthalate and, particularly, methacrylic acid copolymers.

Enteric substances may be used to coat a variety of dosage forms. There are numerous formulation/dosing principles that may be employed in order to prepare dosage forms of the invention and these are described in a non-limiting sense hereinafter.

In this respect, C21 and salts thereof may be presented in any form that is capable of being coated, surrounded and/or encapsulated by an enteric substance to make a final dosage that is suitable for peroral administration to the gastrointestinal tract, and may thus be provided in the form of a powder, a simple mixture, granules, pellets, beads, solutions and/or suspensions. Final dosage forms include pills, tablets, capsules, films, solutions or suspensions (e.g. syrups), powders, cakes and the like.

If C21 or salt thereof is provided in a multiparticulate form as a powder, granules, pellets and/or beads, particles must be coated, either individually or collectively, with an enteric substance. This may be done in a variety of ways.

In this respect, C21 and salts thereof may be presented in the form of a simple mixture with a carrier system, that is any pharmaceutically acceptable inert material that is capable of increasing the mass of a composition, or a component of a composition, in order to provide an appropriately handleable dosage form.

Suitable carriers thus include pharmaceutically acceptable inorganic salts, e.g. sodium chloride, calcium phosphate, dicalcium phosphate hydrate, dicalcium phosphate dehydrate, tricalcium phosphate, calcium carbonate, and barium sulfate; polymers, e.g. (optionally silicified) microcrystalline cellulose, cellulose and crosslinked polyvinylpyrrolidone; starches; sugars and sugar alcohols, e.g. lactose, mannitol, xylitol, isomalt, dextrose; or mixtures of any of the foregoing.

Carrier materials are preferably employed in an amount of between about 5% and about 90% by weight based upon the total weight of the composition comprising C21 or salt thereof to be coated. A preferred range is from about 10% to about 80% by weight.

Preferred carrier materials include lactose, xylitol, isomalt, microcrystalline cellulose and, more preferably, mannitol. Carrier particles may comprise physical mixtures of any of the aforementioned materials and/or may comprise composites of one or more of these materials.

Mixtures of C21/salt with carrier materials mixtures may thereafter be filled directly into capsules prior to application of the enteric substance. Such mixtures may alternatively be granulated into pellets, granules or beads, which secondary particles may be individually coated with an enteric substance, or may be loaded into an appropriate capsule prior to coating with an enteric substance. Powders, pellets, granules or beads may alternatively be compressed into tablets prior to coating with an enteric substance.

Granulation may be carried out using well known techniques, including dry granulation, wet granulation, melt granulation, thermoplastic pelletising, spray granulation or extrusion/spheronization.

Powders, granulates, pellets or beads comprising C21 or salt thereof may, in addition to a carrier material, also comprise other, commonly employed pharmaceutical additives and/or excipients that are used in the art (see, for example Rowe et al, *Handbook of Pharmaceutical Excipients,* 8th ed. (2017) and the documents cited therein).

Other pharmaceutically acceptable excipients are known to those skilled in the art, such as binders, disintegrants, glidants, lubricants and the like.

Binders may be defined as materials that are capable of acting as bond formation enhancers, which may facilitate the compression of a powder mass into coherent compacts. Suitable binders include polyvinylpyrrolidone, gelatin, sodium alginate, cellulose derivatives, such as low substituted hydroxypropyl cellulose, hydroxypropyl methylcellulose, cellulose gum, (optionally silicified) microcrystalline cellulose, and the like. If present, binder is preferably employed in an amount of between about 2% and about 50% by weight based upon the total weight of the composition comprising C21 or salt thereof. A preferred range is from about 5% to about 30% by weight.

Disintegrants or disintegrating agents may be defined as materials that are capable of accelerating to a measurable degree the disintegration/dispersion of a component of a composition comprising C21 or salt thereof, such as a granule or a tablet. This may be achieved, for example, by the material being capable of swelling and/or expanding when placed in contact with aqueous media (particularly bodily fluids including those found in the gastrointestinal tract), thus causing at least part of a dosage form of the invention to disintegrate when so wetted. Suitable disintegrants include cross-linked polyvinylpyrrolidone, cross-linked sodium carboxymethylcellulose (croscarmellose, e.g. Ac-Di-Sol, FMC Corp., USA), carboxymethyl starch, natural starch, pre-gelatinised starch, corn starch, potato starch, sodium starch glycolate (Primojel®, DMV International BV, Netherlands), low substituted hydroxypropyl cellulose and the like. Disintegrant (which may comprise one or more of the materials mentioned above) is preferably employed in an amount of between about 1% (e.g. about 5%) and about 40% by weight based upon the total weight of the composition comprising C21 or salt thereof. A preferred range is from about 5% (e.g. about 10%) to about 30% by weight. Preferred disintegrants that are employed include cross-linked polyvinylpyrrolidone, cross-linked sodium carboxymethylcellulose, sodium starch glycolate and, particularly, low substituted hydroxypropyl cellulose.

Glidants are pharmaceutically-acceptable materials that promote powder flow by reducing interparticle friction and/or cohesion (but does not necessarily have an ability to reduce and/or prevent adhesion to external materials, such as capsule filling machines or hoppers). Suitable pharmaceutically-acceptable glidant materials thus include talc, magnesium carbonate or calcium silicate although it is preferred that the glidant is a hydrophilic glidant, such as one or more of the various forms of silica, including fumed/pyrogenic silica or, more particularly, silica gels, silica aerogels and/or colloidal silica.

Lubricants are typically employed when the final dosage form to be swallowed is in the form of a tablet and prevent granules or powders from adhering to punch die/faces and promote smooth ejection from the die after compaction. Suitable lubricants include stearic acid, sodium stearyl fumarate, anhydrous colloidal silica, talc or, preferably, magnesium stearate). When a lubricant is employed it should be used in very small amounts (e.g. up to about 3%, and preferably up to 2%, by weight based upon the total weight of the composition comprising C21 or salt thereof).

Other excipients that may be employed in oral dosage forms include surfactants, wetting agents, flavourings (e.g. lemon, menthol or peppermint powder), sweeteners (e.g. neohesperidin, sucralose or acesulfame potassium), dyestuffs, antioxidants (which may be naturally occurring or otherwise (e.g. butylated hydroxytoluene (BHT), vitamin C, vitamin E, β-carotene, uric acid, uniquion, superoxide dismutase (SOD), glutathione peroxidase or peroxidase catalase)), preservatives and buffering agents.

These, and the other pharmaceutically-acceptable excipients mentioned herein, may be commercially-available or otherwise are described in the literature, for example, including, for all of these types of excipient, those described in for example, Rowe et al., supra and Remington *The Science and Practice of Pharmacy,* 21st ed., Lippincott Williams and Wilkins, Philadelphia (2006) and the documents referred to therein, the relevant disclosures in all of which documents are hereby incorporated by reference. Otherwise, the preparation of suitable peroral formulations may be achieved non-inventively by the skilled person using routine techniques.

Granules, pellets or beads may be further processed following formation. For example, dry granulates may be broken, ground or milled using a suitable milling technique to produce particulate material of a smaller size, which may also be sieved to separate the desired size fraction. Wet granulates may be screened to break up agglomerates of granules and remove fine material. In either case, the unused undersized (fine), and oversized, material may be reworked to avoid waste.

However, the powder mixture, granulate, tablet or capsule is made prior to coating with the enteric substance, the preparation of the composition to be coated ensures that C21 or pharmaceutically-acceptable salt thereof is homogeneously distributed throughout the carrier material (and/or other excipients that is/are employed).

For simple mixtures, this includes mixing for a time period that provides for a homogeneously-distributed active ingredient, for example as described hereinafter. This is likely to vary according to the equipment used.

The terms 'homogeneous' and 'distributed homogeneously' in the context of the invention mean that there is a substantially uniform content of C21 or salt thereof throughout the carrier material (and/or other excipients that is/are employed). In other words, if multiple (e.g. at least, 2, more preferably about 6, such as about 10 up to about 30 or more if needed) samples are taken from a mixture comprising active ingredient and carrier blend, the measured content of active ingredient that is present as between such samples gives rise to a standard deviation from the mean amount (i.e. the coefficient of variation and/or relative standard deviation) of less than about 8%, such as less than about 6%, for example less than about 5%, particularly less than about 2%.

Preferred mixing equipment include standard mixing equipment, such as tumbler, shaker mixing (e.g. Turbula), convective, hopper, and fluidization blenders. Preferred blenders include V-blenders.

Tablets may be formed by a process of compression/compaction. Direct compression/compaction may be achieved using techniques such as those described in, for example, *Pharmaceutical Dosage Forms: Tablets. Volume 1, 3$^{rd}$ Edition*, Augsburger et al (eds.), CRC Press (2008) and the documents cited therein. Suitable compacting equipment includes standard tabletting machines, such as the Kilian SP300 or the Korsch EK0.

It is preferred that the composition comprising C21 or salt thereof is contained within a capsule that is suitable for such peroral administration.

Appropriate pharmaceutically-acceptable capsules include soft-shell or hard-shell capsules, which can be made from gelatin, cellulose polymers, e.g. hydroxypropyl methylcellulose (HPMC or hypromellose), hypromellose acetate succinate (HPMCAS), starch polymers, pullulan or other suitable materials, for example by way of standard capsule filling processes.

When the dosage form of the invention comprises a solid formulation comprising a mixture of C21 or salt thereof along with carrier materials (e.g. in the form of a powder, granules and the like), in accordance with a preferred aspect of the invention, capsules are preferably hard-shell, two-piece capsules, for example capsules that are made from gelatin or, more preferably, HPMC and are supplied as closed halves that may be separated and filled with particulate matter, followed by re-assembly. Such capsules may be of any size (e.g. 00 to 5), but preferred capsule sizes are size 2, size 1 or, more preferably, size 0.

In this, and other, preferred embodiments of the invention, C21 or salt thereof is presented in the form of particles, which may be amorphous or crystalline or a mixture of the two. Preferred particles are of a size that will not lead to segregation, either during formation of the composition to be loaded into capsules during the capsule-loading process or upon storage.

In this respect, C21 or salt thereof may be provided in the form of a plurality of primary (i.e. non-agglomerated) particles typically having a weight- and/or a volume-based mean diameter of no more than about 1,000 µm, such as about 500 µm, including about 250 µm, preferably no more than about 100 µm, including no more than about 50 µm, such as about 20 µm, or no more than about 10 µm. Although there is no lower limit on particle sizes that may be employed in accordance with the invention, for ease of manufacture, we prefer that primary particles of C21 or salt thereof have weight- and/or volume-based mean diameter of no less than about 1 µm, such as about 2 µm, including about 3 µm.

As used herein, the term 'weight based mean diameter' will be understood by the skilled person to include that the average particle size is characterised and defined from a particle size distribution by weight, i.e. a distribution where the existing fraction (relative amount) in each size class is defined as the weight fraction, as obtained by e.g. sieving (e.g. wet sieving). The term 'volume based mean diameter' is similar in its meaning to weight based mean diameter, but will be understood by the skilled person to include that the average particle size is characterised and defined from a particle size distribution by volume, i.e. a distribution where the existing fraction (relative amount) in each size class is defined as the volume fraction, as measured by e.g. laser diffraction. Particle sizes may also be measured by standard equipment, such as a dry particle size measurement technique, including dry dispersion technologies available from manufacturers such as Sympatec GMbH (Clausthal-Zellerfeld, Germany). Other instruments that are well known in the field may be employed to measure particle size, such as equipment sold by e.g. Malvern Instruments, Ltd. (Worcestershire, UK), Shimadzu (Kyoto, Japan) and (Elzone, Micromeritics (USA; electrical sensing zone method).

By particles having weight- and/or volume-based mean diameters within the above limits, we include mean diameters of particles when prepared and prior to mixing with the relevant excipients according to the invention, and/or prior to being loaded into capsules. It will be appreciated that some aggregation of primary particles to form secondary particles may occur during handling and/or processing of active ingredient. This should nevertheless be minimised.

C21 or salt thereof may also be provided in the form of particles with a relative narrow particle size distribution (PSD), as measured by standard techniques and art-accepted parameters, including mass median diameter ($D_{50}$; the log-normal mass median diameter), the average particle size by mass and/or the diameter at which 50% of the mass in the cumulative PSD are contained) and/or geometric standard deviation (GSD or a $\sigma_g$ measured by the formula $D_{84.13}/D_{50}$ or $D_{50}/D_{15.78}$, where $D_{84.13}$ and $D_{15.78}$ are respectively the diameters at which 84.13% and 15.78% of the mass are contained, and $D_{50}$ is as hereinbefore defined). Such parameters may be measured and calculated in-process using any appropriate sampling method and particle size measurement technique as described hereinbefore.

It is preferred in this respect that C21 or salt thereof has a PSD with a GSD that is less than about 4, such as less than about 3.

Primary particles of C21 or salt thereof may be prepared by an appropriate technique, such as precipitation, cutting (e.g. by way of dissolution in a supercritical fluid under pressure, followed by rapid expansion), spray drying, or may, if appropriate, be micronized by techniques that are well known to those skilled in the art, such as grinding, dry milling, jet milling, wet milling and/or crushing.

Particles may also be sieved to separate into a desired size fraction, and/or screened to break up agglomerates and/or remove fine material. In either case, unused undersized (fine), and oversized, material may be reworked to avoid waste. Alternatively, particles may be separated into appropriate particle sizes using cyclonic separation, by way of an air classifier, sedimentation, force-field fractionation and/or elutriation.

Although C21 or salt thereof may be selected and/or provided with the aforementioned weight- or volume-based mean diameters, particle sizes, PSDs and/or GSDs using one or more of the above techniques, one of the primary benefits of formulating the compositions that are to be loaded into capsules to form dosage forms of the invention, is that C21 or salt thereof does not require the particle processing techniques that are described above prior to blending with relevant excipients.

In this respect, and as mentioned hereinbefore, we have found that C21 and salts thereof are extremely difficult materials to work with. Part of the issue is the hitherto unreported extreme sensitivity of C21 and salts thereof to the combined presence of light and water.

Furthermore, in particular and as described hereinafter, compatibility studies have revealed that certain standard excipients, when co-mixed with C21 and salts thereof give rise to significant chemical instability of the active ingredient. Furthermore, C21 and salts thereof are formed as needle-like crystals that are sticky and have a tendency to agglomerate. This means that dry mixing with certain standard pharmaceutically-acceptable ingredients is very difficult, and it is not straightforward to produce blends with pharmaceutically-acceptable content uniformities of active ingredient, and/or dose uniformities the same within capsules.

Further, it has been found that micronizing primary particles of active ingredient has also not provided a solution to these problems, as the skilled person might have expected to be the case, and also gives rise to additional problems connected with localised heating and static electricity.

However, we have found that by blending C21 or pharmaceutically-acceptable salt thereof with a pre-mixed blend of carrier particles having a weight- and/or a volume-based mean diameter, and/or a structural (particle) density, that is/are similar to the weight- and/or volume-based mean diameter, and/or the structural (particle) density, of the solid particles of C21, or a pharmaceutically-acceptable salt thereof, and a glidant, it is possible to avoid the aforementioned problems and to provide a composition for loading into capsules in which C21 or salt thereof is not only homogeneously and evenly distributed, ensuring dose homogeneity of active ingredient between capsules following such loading, but is also physically and chemically stable, during and after manufacture, under normal storage conditions, and during use.

Thus, in this, first preferred, aspect of the invention, excipients that are admixed with particles of C21 or pharmaceutically-acceptable salt thereof comprise a blend of at least one type of carrier particles with a weight- and/or a volume-based mean diameter, and/or a structural (particle) density, that is/are similar to the weight- and/or volume-based mean diameter, and/or the structural (particle) density, respectively, of the solid particles of C21, or a pharmaceutically-acceptable salt thereof, and a glidant. Such compositions are then loaded into a capsule that is suitable for peroral administration and is coated with an enteric substance.

The terms 'homogeneous' and 'distributed homogeneously' in the context of this aspect of the invention are as hereinbefore defined.

In this preferred aspect of the invention, suitable carrier particle materials may comprise pharmaceutically-acceptable substances that are soluble in water, including carbohydrates, such as sugar alcohols, such as sorbitol, xylitol and, particularly, mannitol. Again, carrier particles may comprise physical mixtures of any of these materials and/or may comprise composites of one or more of these materials.

The carrier particles have a similar particle size distribution and/or structural (particle) density as the active ingredient particles that are employed in compositions to be loaded into capsules to make dosage forms of the invention.

By 'similar particle size distribution and/or structural (particle) density' we mean that the weight- and/or volume-based mean diameter, and/or particle density, of the carrier particles is within about ±75%, such as about ±50%, including about ±40%, e.g. about ±30%, or about ±20% including about ±10% of the relevant dimensions of the C21 or salt thereof that is employed.

In this respect, preferred carrier particle sizes include weight- and/or a volume-based mean diameter that are less than about 100 µm, including less than about 80 µm, such as less than about 70 µm, for example between about 20 µm and about 60 µm (e.g. about 25 µm or, more preferably, about 50 µm).

We have found that, by employing carrier particles with sizes that are similar to those of the active ingredient and/or within the above ranges, blend segregation is avoided.

Thus, to make compositions to be loaded into capsules to make dosage forms in accordance with this aspect of the invention, prior to mixing with active ingredient, carrier particles of the requisite size are pre-blended with a suitable glidant material, preferably a proprietary silica produced under registered trademark 'Syloid®' (see https://grace.com/pharma-and-biotech/en-us/Documents/Syloid/M309c), a colloidal silica, and/or fumed/pyrogenic silica. Preferred forms of silica thus include stable aqueous dispersions (sols) of amorphous silica particles with a weight- and/or a volume-based mean diameter that is between about 1 nm and about 100 nm (e.g. up to about 50 nm, such as up to about 20 nm, such as between about 10 nm and about 15 nm).

It is preferred therefore that the glidant and the carrier particles are mixed together to form an interactive (or an ordered) mixture of carrier particles that are largely coated with smaller particles of a glidant material, which blend is then admixed with active ingredient particles.

We have also found that by adding the aforementioned glidant to the carrier particles to first form an excipient blend, prior to mixing with active ingredient, this improves the flow properties of that excipient blend, and so leads subsequently to better mixing with C21 or pharmaceutically-acceptable salt thereof, further decreasing the likelihood of blend segregation.

In this aspect of the invention, dosage forms may also include other excipients that are well known to those skilled in the art for peroral delivery of active ingredients, such as those mentioned hereinbefore.

However, in view of the extreme sensitivity of C21 and salts thereof to other chemicals, it is preferred that such other excipients are not included in dosage forms according to this aspect of the invention. In this respect, there is provided a dosage form of the invention consisting essentially of a pharmaceutical composition in the form of a particulate mixture comprising solid particles of C21, or a pharmaceutically-acceptable salt thereof, admixed with a blend of carrier particles with a weight- and/or a volume-based mean diameter, and/or a structural (particle) density, that is/are similar to the weight- and/or volume-based mean diameter, and/or the structural (particle) density, of the solid particles of C21, and a glidant, which composition is contained within a capsule that is suitable for such peroral administration and is coated with an enteric substance.

All preferred features mentioned herein for other aspects of the invention which relate in any way to this aspect of the invention are equally applicable.

The term 'consisting essentially of' will be understood to mean that the scope of this (and only this) aspect of the invention is limited to the specified essential features mentioned above, along with other features that do not materially affect the basic and novel characteristic(s) of this aspect of the invention.

In this respect, although not an essential feature of this preferred aspect of the invention, it may be preferable to add a lubricant (such as sodium stearyl fumarate or, preferably, magnesium stearate) to the blend prior to filling into capsules, in order to prevent the blend from adhering to equipment (e.g. capsule filling machines and hoppers). This is a preferred feature that does not materially affect the basic and novel characteristics of this aspect of the invention.

Compositions to be loaded into a capsule that 'consist essentially of' a particulate mixture comprising solid particles of C21, or pharmaceutically-acceptable salt thereof, admixed with a blend of carrier particles as defined above and a glidant may alternatively mean that the composition comprises at least about 95%, such as at least about 97% by weight of those particular ingredients in total.

In this first preferred aspect of the invention, it is also preferred that the dry mix blend is passed through a sieve at points during the mixing process in order to break up agglomerates that are formed during the blending process, for example as described hereinafter. A suitable sieve is one that has a pore size that is of a size that is as small (or thereabouts) as the particle size of the largest component of the blend. Thus, suitable sieve sizes are about 50 µm, e.g. 75 µm, including 100 µm, such as 150 µm, 200 µm or 250 µm (e.g. about 300 µm) up to about 1,000 µm, such as about 400 µm (e.g. about 500 µm) up to about 900 µm (e.g. about 800 µm).

In accordance with a second preferred aspect of the invention, there is provided a dosage form of the invention in which the pharmaceutical composition is presented in the form of a heterogeneous mixture comprising solid particles of C21, or a pharmaceutically-acceptable salt thereof, suspended in a pharmaceutically-acceptable, hydrophobic, lipid-based carrier in which C21 or salt thereof is essentially insoluble, which composition is loaded into a capsule that is suitable for such peroral administration and is coated with an enteric substance.

Lipid-based carrier systems within which solid particles of C21 or salt thereof are suspended may be in the form of solids at room temperature (fats) or, more preferably, may in the form of liquids at room temperature (oils). Particles of C21 or salt thereof may nevertheless be suspended in either form of lipid carrier.

In accordance with this preferred aspect of the invention, we prefer that the capsules are soft-shell, single-piece capsules, for example soft gelatin capsules, in which a single-piece gelatin capsule is filled with a lipid-based suspension of C21 or salt thereof, and thereafter sealed hermetically as a single piece, for example with a drop of gelatin solution. Gelatin may be obtained from any source (e.g. porcine and bovine sources), but it should be noted that there are vegan alternatives to soft gelatin capsules.

Soft gelatin capsule shells may comprise one or more plasticisers, such as xylitol, sorbitol, polyglycerol, non-crystallizing solutions of sorbitol, glucose, fructose and glucose syrups, more preferably glycerin/glycerol, sorbitol and/or proprietary plasiticizers, such as Anidrisorbs (proprietary mixtures of sorbitol, sorbitans, maltitol and mannitol, Roquette Freres, including Anidrisorb 85/70 (a liquid sorbitol-mannitol-hydrolyzed starch plasticizer)). Soft gelatin capsule shells optionally comprise one or more flavouring agents, colouring agents and/or opacifiers (such as titanium dioxide).

Such capsules may be of any shape (e.g. oblong, round, oval, tubular, etc.) and of any size (e.g. 3 to 24 oblong, 1 to 20 round, 2 to 20 oval, 5 to 120 tube, etc.). Preferred capsule sizes will hold a volume of between about 0.3 and about 1.0 mL.

It is an essential feature of this preferred aspect of the invention that C21 or pharmaceutically-acceptable salt thereof is essentially insoluble within the lipid-based carrier under normal storage conditions. By 'essentially insoluble' we include that C21 or salt thereof has a solubility within that carrier that is no more than about 0.015 mg of C21 or salt thereof per gram of carrier.

In this way, because of the carrier's dual properties of hydrophobicity and lack of propensity to dissolve C21 or salt thereof, the active ingredient is not exposed to amounts of water that may catalyze its degradation as described hereinbefore.

We have found, surprisingly, that there are relatively few lipid-based carrier materials that meet these requirements and are therefore able to stabilize C21 or salts thereof at ambient temperatures in dosage forms of the invention.

Hydrophobic lipid-based carrier materials in which C21 or salt thereof must be insoluble as hereinbefore defined may comprise a non-polar oil or fat that is essentially non-miscible with water. It is preferred that the lipid-based carrier is mainly comprised of triacylglycerols (also known as 'triglycerides'), which are esters formed by reaction of all three hydroxyl groups of a glycerol moiety with fatty (carboxylic) acids.

Lipids may thus contain saturated or unsaturated chain fatty acids, which chain can range from 1 carbon atom up to 30 carbon atoms, including up to 26 carbon atoms, such as up to 22 carbon atoms, including 8, 10, 12, 14, 16, 18 or carbon atoms, etc.

Saturated fatty acids that may be mentioned include acetic acid (2), propionic acid (3), butyric acid (4), valeric acid (5), caproic acid (6), enanthic acid (7), caprylic acid (8), pelargonic acid (9), capric acid (10), undecylic acid (11), lauric acid (12), tridecylic acid (13), myristic acid (14), pentadecylic acid (15), palmitic acid (16), margaric acid (17), stearic acid (18), nonadecylic acid (19), arachidic acid (20), heneicosylic acid (21), behenic acid (22), tricosylic acid (23), lignoceric acid (24), pentacosylic acid (25), cerotic acid (26), carboceric acid (27), montanic acid (28), nonacosylic acid (29) and melissic acid (30), wherein the numbers in brackets are the number of carbon atoms in the fatty acid molecule.

Unsaturated fatty acids that may be mentioned include crotonic acid (4:1), as well as ω-3 unsaturated fatty acids, such as octanoic acid (8:1), decanoic acid (10:1), decadienoic acid (10:2), lauroleic acid (12:1), laurolinoleic acid (12:2), myristovaccenic acid (14:1), myristolinoleic acid (14:2), myristolinolenic acid (14:3), palmitolinolenic acid (16:3), hexadecatrienoic acid (16:3), palmitidonic acid (16:

4), α-linolenic acid (18:3), stearidonic acid (18:4), 11,14, 17-eicosatrienoic acid (20:3), eicosatetraenoic acid (20:4), eicosapentaenoic acid (20:5), heneicosapentaenoic acid (21: 5), clupanodonic acid (22:5), docosahexaenoic acid (22:6), 9,12,15,18,21-tetracosapentaenoic acid (24:5), herring acid (24:6) and 6,9,12,15,18,21-tetracosahexaenoic acid (24:6); ω-5 unsaturated fatty acids, such as myristoleic acid (14:1), palmitovaccenic acid (16:1), α-eleostearic acid (18:3), β-eleostearic acid (trans-18:3), punicic acid (18:3), 7,10,13-octadecatrienoic acid (18:3), 9,12,15-eicosatrienoic acid (20:3) and β-eicosatetraenoic acid (20:4); ω-6 unsaturated fatty acids, such as tetradecenoic acid (14:1), 12-octadecenoic acid (18:1), linoleic acid (18:2), linolelaidic acid (trans-18:2), γ-linolenic acid (18:3), calendic acid (18:3), pinolenic acid (18:3), 11,14-eicosadienoic acid (20:2); dihomo-linoleic acid (20:2), dihomo-γ-linolenic acid (20:3), arachidonic acid (20:4), docosadienoic acid (22:2), adrenic acid (22:4), osbond acid (22:5), tetracosatetraenoic acid (24:4) and tetracosapentaenoic acid (24:5); ω-7 unsaturated fatty acids, such as 5-dodecenoic acid (12:1), 7-tetradecenoic acid (14: 1), palmitoleic acid (16:1), vaccenic acid (18:1), rumenic acid (18:2), paullinic acid (20:1), 7,10,13-eicosatrienoic acid (20:3), 15-docosenoic acid (22:1) and 17-tetracosenoic acid (24:1); ω-9 unsaturated fatty acids, such as hypogeic acid (16:1), oleic acid (18:1), elaidic acid (trans-18:1), gondoic acid (20:1), 8,11-eicosadienoic acid (20:2), erucic acid (22: 1), nervonic acid (24:1), mead acid (20:3) and ximenic acid (26:1); ω-10 unsaturated fatty acids, such as sapienic acid (16:1); ω-11 unsaturated fatty acids, such as gadoleic acid (20:1); and ω-12 unsaturated fatty acids, such as 4-hexadecenoic acid (16:1), petroselinic acid (18:1) and eicosenoic acid (20:1), wherein the numbers in brackets are, respectively, the number of carbon atoms, and number of unsaturated (i.e. double) bonds, in the fatty acid molecule.

Fatty acids that may be mentioned include caproic acid, caprylic acid, capric acid, lauric acid, myristic acid, palmitic acid, stearic acid, oleic acid, ricinoleic acid, linoleic acid, linolenic acid, eicosenoic acid, behenic acid and erucic acid.

Triglycerides may be naturally-occurring oils or fats, may be semi-synthetic or may be synthetic.

Naturally-occurring oils or fats may be obtained from an animal or, more preferably, vegetable sources, such as seeds, kernels, or fruits.

Naturally-occurring vegetable oils comprise, principally, triglycerides, which are mixtures of glycerides with differing fatty acid chain lengths.

Naturally-occurring pharmaceutically-acceptable oils that fall into this category include sunflower oil, soybean oil, corn oil, grape seed oil, rapeseed oil, sesame oil, almond oil, apricot kernel oil, cotton seed oil, palm kernel oil, castor oil, olive oil, palm oil and coconut oil (for respective compositions see, for example, *Occurrence and Characteristics of Oils and Fats* at pages 47-224 in Padley, Gunstone and Harwood (Eds.), *The Lipid Handbook.*, Chapman & Hall, London, 1994).

When employed in dosage forms of this preferred aspect of the invention, naturally-occurring oils should be pharmaceutical grade and should therefore preferably be refined after extraction from their natural source(s). This may be done using techniques that are well known to those skilled in the art.

Preferred oils include one or more of sesame oil, corn oil, palm kernel oil, coconut oil or soya oil.

Semi-synthetic and synthetic lipid-based carrier systems may be made using techniques that are well known to those skilled in the art, for example separation, interesterification, fat splitting and transesterification (glycerolysis).

Semi-synthetic and synthetic lipid based carrier systems thus include those that are typically in the form of oils, including short chain ($C_1$ to $C_5$) triglycerides (such as triacetin) and medium chain ($C_6$ to $C_{12}$) triglycerides (the primary component of the naturally-occurring oils palm kernel and coconut oils, such as capric triglycerides, more specifically Miglyol 812N); and those that are often in the form of semi-solid fats, including long chain ($C_{14}$ to $C_{22}$) triglycerides (such as Gelicure 43/10).

Whatever form of hydrophobic lipid-based carrier system is employed, it is preferred that the principal component of the carrier system comprises at least about 85% triacylglycerols, more preferably at least about 90% triacylglycerols, and especially at least about 95% triacylglycerols.

Mixtures of any of the above-mentioned naturally-occurring, semi-synthetic and/or synthetic lipid-based carrier materials may be employed.

In this preferred aspect of the invention, C21 or salt thereof is presented in the form of particles, which may be amorphous or crystalline or a mixture of the two. Preferred particles are of a size that will not lead to sedimentation, either during formation of the suspension, the capsule loading process or upon storage.

In this respect, C21 or salt thereof may be provided for suspension in the lipid-based carrier in the form of a plurality of primary (i.e. non-agglomerated) particles typically having a weight- and/or a volume-based mean diameter (as hereinbefore defined) with the same ranges and values as those described herein for the first preferred aspect of the invention.

By particles having weight- and/or volume-based mean diameters within the aforementioned limits, we include that mean diameters of particles when prepared and prior to suspension in the lipid-based carrier, when so suspended and/or prior to being loaded into capsules as described herein. Primary particles of C21/salt thereof may thus be prepared as described hereinbefore.

It is important to ensure that, prior to loading of the suspension of this second preferred aspect of the invention into capsules, it comprises C21 or salt thereof homogenously and evenly distributed throughout the suspension, to ensure dose homogeneity of active ingredient following such loading into capsules. Accordingly, C21 and salts thereof are preferably provided in the form of particles with a relative PSD as hereinbefore defined.

Although C21 or salt thereof may be selected and/or provided with such a PSD and/or GSD using one or more of the above techniques to provide a stable suspension with an even distribution of C21/salt particles within that suspension, it is important to ensure thorough mixing of C21/salt with the lipid-based carrier system to ensure that an even distribution of active ingredient particles within the carrier is provided prior to loading. This is particularly so in the case of a bulk suspension that is employed as part of a capsule-loading process, where it is important to ensure that the mixture is homogeneous, not only at the outset, but also that this homogeneity is retained during the loading process to ensure dose homogeneity within a production batch.

The terms 'homogeneous' and 'distributed homogeneously' mean that there is a substantially uniform content of C21 or salt thereof throughout the lipid-based carrier material, and are defined hereinbefore.

If the lipid-based carrier system is in the form of a fat (i.e. a solid or a semi-solid at or around normal manufacturing temperatures and/or product storage temperatures), the skilled person will appreciate that the fat will need to be melted by raising the temperature prior to mixing.

Further, in order to ensure that such a suspension provides for a stable, homogeneous even distribution of active ingredient within the carrier, if necessary, the lipid-based carrier system (and particularly those that are in the form of an liquid oil at or around normal manufacturing temperatures and/or product storage temperatures) may further comprise a thickening agent to avoid particle aggregation and/or sedimentation, such as microcrystalline cellulose and carboxymethylcellulose sodium, as well as blends of mono, di- and triglycerides with PEG esters of unsaturated fats, such as Gelucire 43/01, hydrogenated vegetable oil, beeswax, paraffin wax, etc.

By presenting C21, or salt thereof, in the form of a suspension of particles in accordance with this aspect of the invention, we have found that dosage forms of the invention are not only capable of delivering a consistent and/or uniform dose of active ingredient, but also that it is possible to ensure that the active ingredient remains in a form in which it is both physically and chemically stable during and/or after manufacture, under normal storage conditions, and/or during use.

As employed herein, C21, or pharmaceutically-acceptable salt thereof, can be made and stored in the form of composition that may be directly loaded into capsules to make a dosage form of the invention, and furthermore, once made, dosage forms of the invention may be stored under normal storage conditions, with an insignificant degree of changes in physico-chemical properties of the dosage form, composition mixture contained therein and/or, most importantly, active ingredient, over time.

An 'insignificant degree of changes in physico-chemical properties' thus includes that compositions comprising C21/salt in an appropriate carrier as hereinbefore described, before and after having been loaded into capsules and thus in the form of a dosage form of the invention, possess both physical stability and chemical stability.

By 'chemical stability', we include that compositions comprising C21/salt in an appropriate carrier, and dosage forms of the invention, may be stored (with or without appropriate pharmaceutical packaging), under normal storage conditions, with an insignificant degree of chemical degradation or decomposition of the dosage forms of the invention and/or suspensions contained therein, and particularly the active ingredient.

By 'physical stability', we include that suspensions comprising C21/salt in an appropriate carrier, and dosage forms of the invention, may be stored (with or without appropriate pharmaceutical packaging), under normal storage conditions, with an insignificant degree of physical transformation, such as aggregation, separation or segregation, or sedimentation, as described above, or changes in the nature and/or integrity of the dosage forms of the invention and/or compositions contained therein, and particularly the active ingredient, including dissolution, solvatisation, solid state phase transition, etc.

Examples of 'normal storage conditions' include temperatures of between minus 80 and plus 50° C. (preferably between 0 and 40° C. and more preferably ambient temperature, such as between 15 and 30° C.), pressures of between 0.1 and 2 bars (preferably atmospheric pressure), relative humidities of between 5 and 95% (preferably 10 to 60%), and/or exposure to 460 lux of UV/visible light, for prolonged periods (i.e. greater than or equal to six months).

Under such conditions, C21, salt thereof, and/or compositions containing them, may be found to be less than about 15%, more preferably less than about 10%, and especially less than about 5%, physically and/or chemically transformed. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

It is preferred that the pharmaceutical compositions, whether in the form of a dry powder mixture, a lipid-based suspension or otherwise, and/or whether contained within a capsule as described above or otherwise, are manufactured and/or stored in a manner in which they are kept essentially free of water.

By 'essentially free of water', we include that appropriate precautions are taken to ensure that both particles C21 or salt thereof, and the excipients with which it is mixed, are individually prepared and/or provided in a manner in which they are essentially dry, and are also mixed together to form dry mixture in an environment in which they are kept essentially dry.

By 'essentially dry' or 'essentially free of water', we include that the composition comprising C21/salt and relevant excipients comprises, as a whole, no more that about 5%, including no more than about 2%, such as no more than about 1%, including no more than about 0.5%, such as about 0.1% water or less.

Further processing of compositions comprising C21 or salt thereof and relevant excipients into dosage forms of the invention as described hereinbefore may also preferably take place in a manner in which it is kept in such an essentially water-free state.

In this respect, although pharmaceutically-acceptable capsule materials may contain residual amount of water, ingress of water into the composition (whether in the form of a solid (e.g. a powder mixture) or a liquid (e.g. an lipid suspension)) from the capsule material should be minimised, so protecting the highly sensitive C21 or salt thereof from contact with water and therefore, in the presence of light, degradation.

It is nevertheless preferred (although not necessarily essential) to package dosage forms of the invention in a manner that keeps the dosage form itself dry and protected from light. This may include hermetically-sealed packaging, use of deliquescent materials, etc.

According to a further aspect of the invention there is provided a process for the production of a dosage form of the invention, which process comprises coating a composition comprising C21 or a pharmaceutically-acceptable salt thereof with an enteric substance.

Pharmaceutically-acceptable salts of C21 include acid addition salts. Such salts may be formed by conventional means, for example by reaction of C21 in the form of the free acid (hereinafter 'free C21') with one or more equivalents of an appropriate acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of an active ingredient in the form of a salt with another counter-ion, for example using a suitable ion exchange resin. Preferred salts of C21 include HCl salts, alkaline earth salts, such as magnesium and calcium salts, and alkali metal salts, such as potassium or, preferably, sodium salts.

The amount of C21 or salt thereof in a dosage form of the invention will depend, and/or may be selected depending, upon the severity of the condition, or the expectation of such severity, as well as on the patient, to be treated, but may be determined by the skilled person. The mode of administration may also be determined by the timing and frequency of administration, as well as the severity of the condition.

Suitable lower daily doses of C21 in adult patients (average weight e.g. 70 kg), may be about 10 mg, such as about 20 mg, for example about 25 mg, per day. Suitable upper limits of daily dose ranges of C21 may be about up to about 900 mg, such as 600 mg, including about 400 mg and about 200 mg, such as about 100 mg, and including about 50 mg.

All of the above doses are calculated as free C21. Doses may be split into multiple individual doses per day. Doses may be given between once and six, such as four times daily, preferably three times daily and more preferably twice daily.

In any event, the medical practitioner, or other skilled person, will be able to determine routinely the actual dosage, which will be most suitable for an individual patient, depending on the severity of the condition and route of administration. The above-mentioned dosages are exemplary of the average case; there can, of course, be individual instances where higher or lower dosage ranges are merited, and such are within the scope of this invention.

The dose administered to a patient, in the context of the present invention should be sufficient to effect an appropriate response in the patient over a reasonable timeframe (as described hereinbefore). One skilled in the art will recognize that the selection of the exact dose and composition and the most appropriate delivery regimen will also be influenced by inter alia the pharmacological properties of the formulation, the nature, stage and/or severity of the condition being treated, the physical condition and mental acuity of the recipient, including the age, condition, body weight, sex and response of the patient to be treated, and the stage/severity of the disease, and genetic differences between patients.

Dosage forms of the invention are useful in conditions where AT2 receptors are expressed and their stimulation is desired or required.

In this respect, dosage forms of the invention are indicated in the treatment of conditions characterised by vasoconstriction, fibrosis, inflammation, increased cell growth and/or differentiation, increased cardiac contractility, increased cardiovascular hypertrophy, and/or increased fluid and electrolyte retention, as well as skin disorders and musculoskeletal disorders.

Dosage forms of the invention are particularly indicated in the treatment and/or prevention of ILDs, such as sarcoidosis or fibrosis, more specifically PF and particularly IPF, as well as conditions that may trigger ILDs, such as systemic sclerosis, rheumatoid arthritis, myositis or systemic lupus erythematosus, or are otherwise associated with ILDs, such as pulmonary hypertension and/or pulmonary arterial hypertension.

Dosage forms of the invention may also exhibit thromboxane receptor activity. In this respect, dosage forms of the invention may have an inhibitory effect on platelet activation and/or aggregation (and thus e.g. an antithrombotic effect), and/or may reduce vasoconstriction and/or bronchoconstriction in a therapeutic manner.

Dosage forms of the invention are further indicated in the treatment of stress-related disorders, and/or in the improvement of microcirculation and/or mucosa-protective mechanisms.

Thus, dosage forms of the invention are expected to be useful in the treatment of disorders, which may be characterised as indicated above, and which are of, for example, the gastrointestinal tract, the cardiovascular system, the respiratory tract, the kidneys, the immune system. the eyes, the female reproductive (ovulation) system and the central nervous system (CNS).

Disorders of the gastrointestinal tract that may be mentioned include oesophagitis, Barrett's oesophagus, gastric ulcers, duodenal ulcers, dyspepsia (including non-ulcer dyspepsia), gastro-oesophageal reflux, irritable bowel syndrome (IBS), inflammatory bowel disease (IBD), pancreatitis, hepatic disorders (such as hepatitis), gall bladder disease, multiple organ failure (MOF) and sepsis. Other gastrointestinal disorders that may be mentioned include xerostomia, gastritis, gastroparesis, hyperacidity, disorders of the bilary tract, coelicia, Crohn's disease, ulcerative colitis, diarrhoea, constipation, colic, dysphagia, vomiting, nausea, indigestion and Sjögren's syndrome.

Disorders of the respiratory tract that may be mentioned include inflammatory disorders, such as asthma, obstructive lung diseases (such as chronic obstructive lung disease), pneumonitis, pulmonary hypertension, and adult respiratory distress syndrome.

Disorders of the kidneys that may be mentioned include renal failure, diabetic nephropathy, nephritis and renal hypertension.

Disorders of the eyes that may be mentioned include diabetic retinopathy, premature retinopathy and retinal microvascularisation.

Disorders of the female reproductive system that may be mentioned include ovulatory dysfunction and endometriosis.

Cardiovascular disorders that may be mentioned include hypertension, cardiac hypertrophy, cardiac failure (including heart failure with preserved ejection fraction), artherosclerosis, arterial thrombosis, venous thrombosis, endothelial dysfunction, endothelial lesions, post-balloon dilatation stenosis, angiogenesis, diabetic complications, microvascular dysfunction, angina, cardiac arrhythmias, claudicatio intermittens, preeclampsia, myocardial infarction, reinfarction, ischaemic lesions, erectile dysfunction and neointima proliferation.

Disorders of the CNS that may be mentioned include cognitive dysfunctions, dysfunctions of food intake (hunger/satiety) and thirst, stroke, cerebral bleeding, cerebral embolus and cerebral infarction, multiple sclerosis (MS), Alzheimer's disease and Parkinson's disease.

Dosage forms of the invention may also be useful in the modulation of growth metabolism and proliferation, for example in the treatment of ageing, hypertrophic disorders, prostate hyperplasia, autoimmune disorders (e.g. arthritis, such as rheumatoid arthritis, or systemic lupus erythematosus), psoriasis, obesity, neuronal regeneration, the healing of ulcers, inhibition of adipose tissue hyperplasia, stem cell differentiation and proliferation, fibrotic disorders, cancer (e.g. in, or of, the gastrointestinal tract (including the oesophagus or the stomach), the prostate, the breast, the liver, the kidneys, as well as lymphatic cancer, lung cancer, ovarian cancer, pancreatic cancer, hematologic malignancies, etc.), apoptosis, tumours (generally) and hypertrophy, diabetes, neuronal lesions and organ rejection.

Dosage forms of the invention are also useful in the treatment of stroke, spinal cord injury, sickle cell disease, muscular dystrophy, cancer treatment-related cardiotoxicity, peripheral neuropathy and, in particular, systemic sclerosis.

In addition, dosage forms of the invention may be useful in the treatment of respiratory virus-induced tissue damage, which damage may include injury and/or dysfunction of relevant tissues. Relevant tissues include (e.g. mucosal) tissues of the respiratory tract, and especially those of the lung. Relevant tissue thus includes the respiratory epithelium, which moistens the airways and protects against invasion of pathogens such as viruses.

Respiratory viruses that may be mentioned in this respect include influenza viruses, such as influenza A virus (e.g. H1N1 and H3N2 viruses), influenza B virus or influenza C virus), and, more particularly, coronaviruses, including severe acute respiratory syndrome (SARS) coronaviruses, such as SARS coronavirus (SARS-CoV) and, particularly, the novel SARS coronavirus 2 (SARS-CoV-2, previously known as '2019-nCoV' or 'novel coronavirus 2019'), which is the virus that causes coronavirus disease 2019 (COVID-19), of which there are many genetic variants.

By 'treatment of tissue damage', we include that C21 and salts thereof may not only have a beneficial effect on tissue damage in the respiratory tract that has been caused by such a virus, but that it may also prevent and/or mitigate the damage that would otherwise have been caused by that virus in the respiratory tract, which occurs when the relevant virus enters e.g. epithelial cells in the respiratory tract.

Thus, C21 and salts thereof may abrogate or prevent the development of diseases that are caused by such virally-induced tissue damage and/or the symptoms of such damage or diseases.

In this respect, C21 and salts thereof may treat, and/or arrest the progress of, diseases that are being, or have been, caused by respiratory viruses (i.e. diseases such as influenza, as well as acute lung injury acute lung injury (ALI), acute respiratory distress syndrome (ARDS), particularly SARS and, more particularly, COVID-19) and their sequelae. C21 and salts thereof may also treat and/or prevent the damage that is being, or has been, caused by such viruses, which includes treating and/or preventing the symptoms of such respiratory diseases, which symptoms include cough, dyspnea, respiratory distress (as manifest by e.g. the need for supplementary/supplemental oxygen (which may be administered by a face mask or via nasal cannula (high flow or otherwise)), and/or mechanical ventilation/extra-corporeal membrane oxygenation), respiratory failure, and/or pneumonia, which may occur directly (viral pneumonia) and/or indirectly (bacterial pneumonia resulting from secondary bacterial infections, which is common in influenza), as well as subsequent fibrosis resulting from inflammation in the lungs and other organs (e.g. the heart and kidneys). Further, C21 and salts thereof may prevent or arrest the progress of respiratory virus-induced morbidity and/or mortality, and C21 may treat, and/or arrest the development of any of the chronic symptoms identified above.

In addition, dosage forms of the invention may also be useful in the treatment or prevention of any fibrotic condition of one or more internal organs characterised by the excessive accumulation of fibrous connective tissue, and/or in the treatment or prevention of fibrogenesis and the morbidity and mortality that may be associated therewith. Such fibrosis may be associated with an acute inflammatory condition, such as acute respiratory distress syndrome (ARDS), SARS, and multiple-organ inflammation, injury and/or failure, which may be caused by internal or external trauma (e.g. injury), or by an infection.

Such conditions may thus result from sepsis or septic shock caused by a viral, bacterial or fungal infection. Furthermore, acute lung injury, ARDS and, particularly, SARS may be caused by viruses, such as coronaviruses, include SARS-CoV-2, which may result in internal tissue damage and/or dysfunction of relevant internal (e.g. mucosal) tissues, and/or the cells that comprise them, such as the respiratory epithelium. Such tissue damage may in turn give rise to severe fibrosis. For example, the SARS disease caused by SARS-CoV-2 (coronavirus disease 2019 or COVID-19) is known in many cases to result in fibrosis.

However, dosage forms of the invention are also especially useful in the treatment or prevention of ILDs as defined herein, including sarcoidosis or fibrosis, more specifically pulmonary fibrosis and particularly IPF, as well as conditions that may trigger ILDs, such as systemic sclerosis, rheumatoid arthritis, myositis or systemic lupus erythematosus, or are otherwise associated with ILDs, such as pulmonary hypertension and/or pulmonary arterial hypertension.

The term 'ILD' will be understood by those skilled in the art to include any pulmonary condition characterized by an abnormal healing response, including chronic inflammation, reduced lung function and/or scarring, irrespective of the cause, such as sarcoidosis, and PF, especially IPF. The term may also include diseases and/or conditions that are known to lead to, and/or be causes of, such pulmonary conditions, such as systemic sclerosis. In this respect there is further provided a dosage form of the invention for use in the condition that leads to and/or is a cause of an ILD, such as PF or IPF, including systemic sclerosis.

In the treatment of PF, including IPF, dosage forms of the invention may have an anti-fibrotic effect, with reduction of fibrosis and prevention of further deposition of extra cellular matrix. Dosage forms of the invention may affect lung scarring/wound healing and also have an anti-apoptotic effect, thereby preventing apoptosis for alveolar endothelial cells, being an initiating factor for the development of PF. Dosage forms of the invention may also have an anti-proliferative effect, thus reducing the cancer-like proliferation of fibroblasts and myofibroblasts in PF. Dosage forms of the invention may also improve vascular remodelling in PF, thereby reducing secondary pulmonary hypertension. Finally, dosage forms of the invention may demonstrate anti-inflammatory and anti-cytokine effects.

According to a further aspect of the present invention, there is provided a method of treatment of any of the aforementioned conditions, including respiratory viral damage and, more particularly, an ILD, including PF, and in particular IPF, which method comprises administration of a therapeutically effective amount of a dosage form of the invention to a person suffering from, or susceptible to, such a condition.

According to a yet further aspect of the present invention, there is provided a method of treatment of respiratory virus-induced tissue damage in a subject, which method comprises administration of a therapeutically effective amount of a dosage form of the invention to a subject in need of such treatment, particularly in which:

the tissue that is damaged is lung tissue, including the respiratory epithelium;

the damage comprises injury and/or dysfunction of the mucosal tissue of the respiratory tract caused by a respiratory virus;

the treatment includes treatment, and/or arresting the progress, of a disease that is being, or has been, caused by the virus;

the respiratory virus is a coronavirus, such as SARS-CoV-2, and the disease is a SARS, such as COVID-19; or the respiratory virus is an influenza virus, and the disease is influenza;

the treatment includes treatment of the symptoms of the disease that is being, or has been, caused by the relevant virus;

the symptoms of the damage or the disease include one or more of cough, dyspnea, respiratory distress (which may be manifest by the need for supplementary oxygen and/or mechanical ventilation), respiratory failure, pneumonia, fibrosis in one or more internal organs, including the lungs, the heart and/or the kidneys; and/or the treatment includes prevention of respiratory virus-induced morbidity and/or mortality in one or more of the foregoing conditions.

The dosage forms of the invention are indicated both in the therapeutic, palliative, and/or diagnostic treatment (e.g. during diagnostic workup if a condition is suspected), as well as the prophylactic treatment (by which we include preventing and/or abrogating deterioration and/or worsening of a condition) of any of the above conditions.

'Patients' include avian and mammalian (particularly human) patients. Human patients include both adult patients as well as pediatric patients, the latter including patients up to about 24 months of age, patients between about 2 to about 12 years of age, and patients between about 12 to about 16 years of age. Patients older than about 16 years of age may be considered adults for purposes of the present invention. These different patient populations may be given different doses of C21 or salt thereof.

It is preferred, in the treatment of certain conditions such as respiratory virus-induced tissue damage, that C21 or a pharmaceutically-acceptable salt thereof is administered to adult patients, more particularly subjects that are over the age of about 20, such as over the age of about 30, including over the age of about 40, more preferably over the age of about 50, especially over the age of about 60, particularly over the age of about 70, and more particularly over the age of about 80 years of age; and/or to patients (whether or not such patients are in one of the age groups specified above) with one or more of the following underlying medical conditions:
 chronic (long-term) respiratory diseases, such as pulmonary fibrosis, pulmonary hypertension, pulmonary arterial hypertension, other ILDs, asthma, chronic obstructive pulmonary disease (COPD), emphysema or bronchitis
 chronic cardiovascular (e.g. heart) disease, such as heart failure, atrial fibrillation or hypertension
 chronic kidney disease
 chronic liver disease, such as hepatitis
 chronic neurological conditions, such as Parkinson's disease, motor neurone disease, multiple sclerosis, a learning disability or cerebral palsy
 diabetes
 problems with a patient's spleen—for example, sickle cell disease or if the spleen has been removed
 a weakened immune system as the result of conditions, such as HIV and AIDS, or medicines such as steroid tablets or chemotherapy
 obesity (e.g. a body mass index (BMI) of 40 or above)
 pregnancy.

In this respect, according to several further aspects of the invention there is provided a method of treatment and/or prevention of one or more the following conditions:
 post-acute sequelae of e.g. SARS-CoV-2 infection (PASO), such as what is known as 'long COVID', 'chronic COVID syndrome' (CCS) and/or long-haul COVID';
 acute kidney injury and/or chronic kidney disease;
 respiratory diseases such as pulmonary fibrosis, pulmonary hypertension, pulmonary arterial hypertension, asthma, chronic obstructive pulmonary disease (COPD), emphysema and/or bronchitis; and
 cardiovascular diseases such as myocardial infarction, heart failure, atrial fibrillation, hypertension or thrombosis and/or embolization in e.g. the heart, lungs and/or brain, all of which may be induced, directly or indirectly, by respiratory viruses (such as SARS-CoV-2), which method comprises administering C21 or a pharmaceutically-acceptable salt thereof to a subject in need of such treatment and/or prevention.

In relation to (for example) acute treatment of respiratory virus-induced tissue damage, doses of C21 or salt thereof may be administered between once and four times (e.g. between 1 and 3 times) daily for up to three (e.g. two) months, such as one month, including up to three weeks, e.g. up to one week, such as 4 days or 3 days. Such treatment periods may be repeated as appropriate.

In the case of the development of one or more of the chronic symptoms identified hereinbefore, such as fibrosis of the lungs and other internal organs, treatment with C21 or salt thereof may, in addition to and/or instead of the above-mentioned acute dosing regimens, be continuous and/or as needed/required.

Relevant active ingredients that may be used in combination therapy with C21 in the treatment of patients with viral infections include more the variously-applied standard treatments for viral infections, including antibody therapies (e.g. LY-CoV555/LY-CoV016 (bamlanivimab and etesevimab), LY-CoV555 (bamlanivimab, Eli Lilly), REGN-COV2 (casirivimab and imdevimab), REGN3048-3051, TZLS-501, SNG001 (Synairgen), eculizumab (Soliris; Alexion Pharmaceuticals), ravulizumab (Ultomiris; Alexion Pharmaceuticals), lenzilumab, leronlimab, tocilizumab (Actemra; Roche), sarilumab (Kevzara; Regeneron Pharma), and Octagam (Octapharma)), antiviral medicines (e.g. oseltamivir, remdesivir, favilavir, molnupiravir, simeprevir, daclatasvir, sofosbuvir, ribavirin, umifenovir, lopinavir, ritonavir, lopinavir/ritonavir (Kaletra; AbbVie Deutschland GmbH Co. KG), teicoplanin, baricitinib (Olumiant; Eli Lilly), ruxolitinib (Jakavi; Novartis), tofacitinib (Xeljanz; Pfizer), the TMPRSS2 inhibitor, camostat, or camostat mesylate, Actembra (Roche), TZLS-501, AT-100 (rhSP-D), MK-7110 (CD24Fc; Merck)), OYA1 (OyaGen9), BPI-002 (Beyond-Spring), NP-120 (Ifenprodil; Algernon Pharmaceuticals), Galidesivir (Biocryst Pharma), antiinflammatory agents (e.g. NSAIDs, such as ibuprofen, ketorolac, naproxen and the like, chloroquine, hydroxychloroquine, interferons (e.g. interferon beta (interferon beta-1a), tocilizumab (Actemra), lenalidomide, pomalidomide and thalidomide), analgesics (e.g. paracetamol or opioids), antitussive agents (e.g. dextromethorphan), vaccinations (e.g. INO-4800 by Inovio Pharmaceuticals and Beijing Advaccine Biotechnology, if available), COVID-19 convalescent plasma (CCP) and/or passive antibody therapy with antibodies from blood of people who have recovered from infection with SARS-CoV or SARS-CoV-2.

Relevant active ingredients that may be used in combination therapy with C21 in the treatment of ILDs, such as IPF include, for example, anti-fibrotics (e.g. nintedanib and, particularly, pirfenidone); vitamins (e.g. vitamin B, C and D); mucolytics (e.g. acetylcysteine and ambroxol); corticosteroids, such as cortisone and prednisone; inflammation suppressants, such as cyclophosphamide; other immunosuppressants, such as azathioprine and mycophenolate mofetil; and antioxidants, such as N-acetylcysteine. Relevant active ingredients that may be used in combination therapy with C21 in the treatment of sarcoidosis include, for example, corticosteroids, such as cortisone, prednisone and prednisolone; antimetabolites; immune system suppressants, such as methotrexate, azathioprine, leflunomide, mycophenoic acid/ mycophenolate mofetil, cyclophosphamide; aminoquinolines; monoclonal anti-tumor necrosis factor antibodies, such as infliximab and adalimumab; immunomodulatory imide drugs, such as include lenalidomide, pomalidomide and, especially, thalidomide; the TNF inhibitor, etanercept; and painkillers, such as ibuprofen and paracetamol; cough suppressants and/or expectorants.

For the avoidance of doubt, 'corticosteroids' as mentioned above include both naturally-occurring corticosteroids and synthetic corticosteroids.

Naturally-occurring corticosteroids that may be mentioned include cortisol (hydrocortisone), aldosterone, corticosterone, cortisone, pregnenolone, progesterone, as well as naturally-occurring precursors and intermediates in corticosteroid biosynthesis, and other derivatives of naturally-occurring corticosteroids, such as 11-deoxycortisol, 21-deoxycortisol, 11-dehydrocorticosterone, 11-deoxycorticosterone, 18-hydroxy-11-deoxycorticosterone, 18-hydroxycorticosterone, 21-deoxycortisone, 11β-hydroxypregnenolone, 11β, 17α,21-trihydroxypregnenolone, 17α,21-dihydroxypregnenolone, 17α-hydroxypregnenolone, 21-hydroxypregnenolone, 11-ketoprogesterone, 11β-hydroxyprogesterone, 17α-hydroxyprogesterone and 18-hydroxyprogesterone.

Synthetic corticosteroids that may be mentioned include those of the hydrocortisone-type (Group A), such as cortisone acetate, hydrocortisone aceponate, hydrocortisone acetate, hydrocortisone buteprate, hydrocortisone butyrate, hydrocortisone valerate, tixocortol and tixocortol pivalate, prednisolone, methylprednisolone, prednisone, chloroprednisone, cloprednol, difluprednate, fludrocortisone, fluocinolone, fluperolone, fluprednisolone, loteprednol, prednicarbate and triamcinolone; acetonides and related substances (Group B), such as amcinonide, budesonide, desonide, fluocinolone cetonide, fluocinonide, halcinonide, triamcinolone acetonide, ciclesonide, deflazacort, formocortal, fludroxycortide, flunisolide and fluocinolone acetonide, those of the (beta) methasone-type (Group C), such as beclomethasone, betamethasone, betamethasone dipropionate and betamethasone valerate, dexamethasone, fluocortolone, halometasone, mometasone and mometasone furoate, alclometasone and alclometasone dipropionate, clobetasol and clobetasol propionate, clobetasone and clobetasone butyrate, clocortolone, desoximetasone, diflorasone, difluocortolone, fluclorolone, flumetasone, fluocortin, fluprednidene and fluprednidene acetate, fluticasone, fluticasone furoate and fluticasone propionate, meprednisone, paramethasone, prednylidene, rimexolone and ulobetasol; those of the progesterone-type, such as flugestone, fluorometholone, medrysone and prebediolone acetate, and progesterone derivatives (progestins), such as chlormadinone acetate, cyproterone acetate, medrogestone, medroxyprogesterone acetate, megestrol acetate and segesterone acetate; as well as other corticosteroids, such as cortivazol and 6-methyl-11β,17β-dihydroxy-17α-(1-propynyl)androsta-1,4,6-trien-3-one.

Preferred corticosteroids include cortisone, prednisone, prednisolone, methylprednisolone and, especially, dexamethasone.

Further, relevant active ingredients that may be used in combination therapy with C21 (e.g. to treat respiratory viral infections) include H2 receptor blockers, anticoagulants, anti-platelet drugs, as well as statins, antimicrobial agents and anti-allergic/anti-asthmatic drugs.

H2 receptor blockers that may be mentioned include famotidine. Anticoagulants that may be mentioned include heparin and low-molecular-weight heparins (e.g. bemiparin, nadroparin, reviparin, enoxaparin, parnaparin, certoparin, dalteparin, tinzaparin); directly acting oral anticoagulants (e.g. dabigatran, argatroban, rivaroxaban, apixaban, edoxaban, betrixaban, darexaban, otamixaban, letaxaban, eribaxaban, hirudin, lepirudin and bivalirudin); coumarin type vitamin K antagonists (e.g. coumarin, acenocoumarol, phenprocoumon, atromentin and phenindione) and synthetic pentasaccharide inhibitors of factor Xa (e.g. fondaparinux, idraparinux and idrabiotaparinux). Anti-platelet drugs that may be mentioned include irreversible cyclooxygenase inhibitors (e.g. aspirin and triflusal); adenosine diphosphate receptor inhibitors (e.g. cangrelor, clopidogrel, prasugrel, ticagrelor and ticlopidine); phosphodiesterase inhibitors (e.g. cilostazol); protease-activated receptor-1 antagonists (e.g. vorapaxar); glycoprotein IIB/IIIA inhibitors (e.g. abciximab, eptifibatide and tirofiban); adenosine reuptake inhibitors (e.g. dipyridamole); and thromboxane inhibitors (e.g. terutroban, ramatroban, seratrodast and picotamide). Statins that may be mentioned include atorvastatin, simvastatin and rosuvastatin. Antimicrobial agents that may be mentioned include azithromycin, ceftriaxone, cefuroxime, doxycycline, fluconazole, piperacillin, tazobactam and teicoplanin. Anti-allergic/anti-asthmatic drugs that may be mentioned include chlorphenamine, levocetirizine and montelukast.

Further relevant active ingredients that may be used in combination therapy with C21 (e.g. to treat respiratory viral infections) include other AT2 agonists that are known in the art as well as in combination with AT1 receptor antagonists that are known in the art, and/or in combination with an inhibitor of angiotensin converting enzyme (ACE). Non-limiting but illustrative examples of AT1 receptor antagonists that can be used according to the embodiments include azilsartan, candesartan, eprosartan, fimasartan, irbesartan, losartan, milfasartan, olmesartan, pomisartan, pratosartan, ripiasartan, saprisartan, tasosartan, telmisartan, valsartan and/or combinations thereof. Non-limiting but illustrative examples of ACE inhibitors that can be used according to the embodiments include captopril, zofenopril, enalapril, ramipril, quinapril, perindopril, lisinopril, benazepril, imidapril, trandolapril, fosinopril, moexipril, cilazapril, spirapril, temocapril, alacepril, ceronapril, delepril, moveltipril, and/or combinations thereof.

Relevant patients may also (and/or may already) be receiving one or more of any of the treatments and/or other therapeutic agents mentioned above for the relevant condition based upon administration of one or more of such active ingredients, by which we mean receiving a prescribed dose of one or more of those active ingredients mentioned herein, prior to, in addition to, and/or following, treatment with C21 or a salt thereof.

Pharmaceutically-acceptable salts, and doses, of other active ingredients mentioned above include those that are known in the art and described for the drugs in question to in the medical literature, such as *Martindale—The Complete Drug Reference*, 38$^{th}$ Edition, Pharmaceutical Press, London (2014 and the documents referred to therein, the relevant disclosures in all of which documents are hereby incorporated by reference.

Dosage forms of the invention have the advantage that they can be manufactured and stored under normal storage conditions, including without freezing and/or being exposed to light, maintaining pharmaceutically-acceptable physicochemical stability of the composition contained with the capsule and, in particular, the active ingredient.

Dosage forms of the invention may also provide for an improved drug loading, enables high quantities/doses of active compound to be presented, and also efficient delivery of such higher doses in a consistent/uniform manner. This in turn enhances the effectiveness and efficiency of treatment and reduces costs for healthcare.

The uses/methods described herein may otherwise have the advantage that, in the treatment of one or more of the conditions mentioned hereinbefore, and in particular ILDs and/or respiratory viral infections, they may be more convenient for the physician and/or patient than, be more efficacious than, be less toxic than, have a broader range of activity than, be more potent than, produce fewer side effects than, or that it may have other useful pharmacological properties over, similar methods (treatments) known in the prior art, whether used in those conditions or otherwise.

Wherever the word 'about' is employed herein, for example in the context of numbers or amounts, i.e. absolute amounts such as sizes (e.g. particle sizes), doses, weights or concentrations of (e.g. active) ingredients, ages, temperatures or time periods; or relative amounts including percentages and standard deviations, it will be appreciated that such variables are approximate and as such may vary by ±10%, for example ±5% and preferably ±2% (e.g. ±1%) from the actual numbers specified. In this respect, the term 'about 10%' means e.g. ±10% about the number 10, i.e. between 9% and 11%.

The invention is illustrated, but in no way limited, by the following examples.

EXAMPLES

Example 1—Observation of Food Effect in a Clinical Setting

A Phase I clinical trial was conducted to evaluate the safety, tolerability, and pharmacokinetics of C21 in healthy male and female subjects. The study design allowed a gradual escalation of dose with intensive clinical data and PK monitoring to ensure the safety and wellbeing of subjects.

The study was designed and conducted in accordance with the CRO's standard operating procedures (SOPs), which comply with the ethical principles laid down in the International Council for Harmonisation (ICH) Good Clinical Practice (GCP) guidance as required by the major regulatory authorities, and in accordance with the Declaration of Helsinki as amended by the 48th General Assembly in October 1996. C21 was found to be safe and generally well tolerated. No serious adverse events were recorded.

In addition, the effect of food on the pharmacokinetics (PK) of C21 was investigated in an open label manner in 10 male and female subjects at a single oral dose of 75 mg.

Subjects were to receive two single doses of 75 mg of C21 at least 3 days apart in a randomised fashion either in fasted or in fed state. A Food and Drug Administration (FDA)-recommended high-fat breakfast was used to investigate maximum effects.

In the food effect part of the study, the subjects' ages ranged from 22 to 44 years with a median age of 36.0 years. Most of the subjects were Caucasian (9 (90.0% of) subjects) and male (8 (80.0% of) subjects). The mean (SD) BMI of overall subjects was 23.96 (2.223) kg/m².

C21 sodium salt as a pre-frozen oral solution (comprising 2.5 mg/mL C21 sodium salt sodium salt dissolved in an aqueous carbonate buffer) with a composition as shown in Table 1 below.

TABLE 1

| Components | Function | Quantity per mL | Quality references standard |
|---|---|---|---|
| Citric acid monohydrate | Buffer component | 2 mg | Ph. Eur. |
| Denatonium benzoate | Flavouring agent | 3 µg | USP-NF |
| Ethanol (96 per cent) | Solvent for denatonium benzoate | Approx. 35 µL | Ph. Eur. |
| Hydrochloric acid | pH regulator | q.s. to pH 2.0-3.5 | Ph. Eur. |
| Sodium hydroxide | pH regulator | q.s. to pH 2.0-3.5 | Ph. Eur. |
| Water, purified | Solvent | to 1.0 mL | Ph. Eur. |

Plasma concentrations below the lower limit of quantification (LLOQ) were presented as below the lower limit of quantification (BLQ). Plasma concentrations for C21 were summarised by study part, dose cohort and nominal time point.

Pharmacokinetic parameters were calculated by non-compartmental analysis methods from the concentration-time data using Phoenix® WinNonlin® (Version 8.0) or higher following these guidelines:

Actual sampling times relative to dosing rather than nominal times were used in the calculation of all derived pharmacokinetic parameters.

There was no imputation of missing data.

Any subjects with missing concentration data were included in the PK analysis set provided that at least $C_{max}$ and $AUC_{(0-t)}$ could be reliably calculated.

All BLQ values pre-dose and in the absorption phase prior to the first quantifiable concentration were substituted by zeros. Single BLQs that fell between two evaluable concentrations were substituted by missing, before the calculation of the PK variables. Consecutive BLQs that fell between evaluable concentrations were substituted by zero, before the calculation of the PK variables. Terminal BLQ values were disregarded.

Bioequivalence of PK parameters from the open label food effect arm were determined by constructing 90% confidence intervals around the estimated difference between the Test and Reference treatments using a mixed effects model based on natural log transformed data. The mixed effects model was implemented using SAS Proc Mixed, with REML estimation method and Kenward-Roger degrees of freedom algorithm.

Natural logarithm transformed $AUC_{(0-inf)}$ (if data permitted), $AUC_{(0-24)}$ and $C_{max}$ were analysed using a mixed effects model with sequence, period and treatment as fixed effects and subject within sequence as a random effect. Estimates of the mean differences (Test-Reference) and corresponding 90% confidence intervals were obtained from the model. The estimated mean differences and 90% confidence intervals for the differences were exponentiated to provide estimates of the ratio of geometric means (Test/Reference) and 90% confidence intervals for the ratios. C21 in the fasted state is the Reference treatment and C21 in the fed state is the Test treatment.

The comparisons assessing the food effect (bioequivalence) were used to assess the effect of food on the rate and extent of absorption of C21 administered under fasted and fed conditions with estimates of the mean differences as well as corresponding 90% confidence intervals being presented.

Pharmacokinetic parameter data for C21 are summarized descriptively in Table 2 below.

TABLE 2

| Parameter (Unit) | Statistic | C21 (75 mg) Fed (N = 10) | C21 (75 mg) Fasted (N = 9) |
|---|---|---|---|
| $C_{max}$ (ng/mL) | n | 10 | 9 |
| | Arithmetic Mean | 269.0 | 1810 |
| | SD | 58.92 | 668.2 |
| | CV % | 21.9 | 36.9 |
| | Geometric Mean | 263.2 | 1708 |
| | Geometric CV % | 22.4 | 37.1 |
| $C_{av}$ (ng/mL) | n | 10 | 9 |
| | Arithmetic Mean | 33.0 | 77.4 |
| | SD | 8.92 | 26.4 |
| | CV % | 27.0 | 34.1 |
| | Geometric Mean | 32.0 | 73.6 |
| | Geometric CV % | 25.7 | 34.1 |
| $t_{max}$ (h) | n | 10 | 9 |
| | Median | 1.26 | 0.670 |
| | Minimum | 0.67 | 0.33 |
| | Maximum | 4.0 | 0.68 |
| $t_{1/2}$ (h) | n | 10 | 9 |
| | Arithmetic Mean | 0.862 | 0.602 |
| | SD | 0.242 | 0.235 |
| | CV % | 28.1 | 39.0 |
| | Geometric Mean | 0.835 | 0.569 |
| | Geometric CV % | 26.6 | 35.4 |
| $AUC_{(0-6)}$ (h*ng/mL) | n | 10 | 9 |
| | Arithmetic Mean | 746.6 | 1853 |
| | SD | 157.8 | 630.5 |
| | CV % | 21.1 | 34.0 |
| | Geometric Mean | 732.0 | 1764 |
| | Geometric CV % | 21.1 | 34.0 |
| $AUC_{(0-12)}$ (h*ng/mL) | n | 10 | 9 |
| | Arithmetic Mean | 790.5 | 1857 |
| | SD | 211.9 | 632.6 |
| | CV % | 26.8 | 34.1 |
| | Geometric Mean | 767.4 | 1767 |
| | Geometric CV % | 25.5 | 34.1 |
| $AUC_{(0-24)}$ (h*ng/mL) | n | 10 | 9 |
| | Arithmetic Mean | 792.0 | 1857 |
| | SD | 214.1 | 632.6 |
| | CV % | 27.0 | 34.1 |
| | Geometric Mean | 768.5 | 1767 |
| | Geometric CV % | 25.7 | 34.1 |
| $AUC_{(0-t)}$ (h*ng/mL) | n | 10 | 9 |
| | Arithmetic Mean | 767.3 | 1841 |
| | SD | 219.9 | 626.8 |
| | CV % | 28.7 | 34.1 |
| | Geometric Mean | 741.5 | 1752 |
| | Geometric CV % | 27.6 | 34.2 |
| $AUC_{(0-inf)}$ (h*ng/mL) | n | 10 | 9 |
| | Arithmetic Mean | 792.0 | 1857 |
| | SD | 214.2 | 632.6 |
| | CV % | 27.0 | 34.1 |
| | Geometric Mean | 768.5 | 1767 |
| | Geometric CV % | 25.8 | 34.1 |
| % $AUC_{ex}$ (%) | n | 10 | 9 |
| | Arithmetic Mean | 3.5 | 0.89 |
| | SD | 2.4 | 0.29 |
| | CV % | 69.0 | 32.2 |
| CL/F (L/h) | n | 10 | 9 |
| | Arithmetic Mean | 100.3 | 44.52 |
| | SD | 23.57 | 14.43 |
| | CV % | 23.5 | 32.4 |
| | Geometric Mean | 97.59 | 42.44 |
| | Geometric CV % | 25.8 | 34.1 |
| $V_z/F$ (L) | n | 10 | 9 |
| | Arithmetic Mean | 120 | 36.6 |
| | SD | 26.2 | 12.4 |
| | CV % | 21.9 | 33.9 |
| | Geometric Mean | 118 | 34.8 |
| | Geometric CV % | 21.0 | 33.9 |

CV %: Coefficient of variation;
SD: Standard deviation.
N: The number of subjects included in the PK Analysis Set for each treatment.

Following oral doses of 75 mg C21, peak plasma concentrations occurred at a median $t_{max}$ of 0.67 and 1.26 hours when administered under fasted and fed conditions, respectively. The geometric mean $C_{max}$ was 1708 ng/mL for 75 mg fasted and 263 ng/mL for 75 mg fed.

Variability (geometric CV %) for $C_{max}$ was 37% and 22% for fasted and fed, respectively. The geometric mean $AUC_{(0-12)}$ was 1767 h*ng/mL and 767 h*ng/mL for 75 mg fasted and fed, respectively. All AUC parameters were comparable for each treatment and geometric CV % for AUC parameters ranged from 21% to 34% for 75 mg fasted and fed. The mean $t_{1/2}$ was less than 1 hour for both fasted and fed treatments. Consistent with measured AUC values, CL/F was approximately 2-fold higher for the fed treatment and $V_z/F$ was 3-fold higher compared to the fasted treatment values.

Statistical analysis of the food effect on C21 is summarized in Table 3.

TABLE 3

| PK Parameter (unit) | Treatment | Geometric Mean (95% CI) | Geometric Mean Ratio (Fed:Fasted) | 90% CI (%) |
|---|---|---|---|---|
| $AUC_{(0-inf)}$ (h*ng/mL) | C21 (75 mg) Fed (N = 10) | 768.52 (642.86, 918.75) | 0.449 | (41.04, 49.04) |
| | C21 (75 mg) Fasted (N = 9) | 1713.18 (1431.01, 2050.98) | | |
| $AUC_{(0-24)}$ (h*ng/mL) | C21 (75 mg) Fed (N = 10) | 768.48 (642.85, 918.66) | 0.449 | (41.03, 49.04) |
| | C21 (75 mg) Fasted (N = 9) | 1713.20 (1431.09, 2050.93) | | |
| $C_{max}$ (ng/mL) | C21 (75 mg) Fed (N = 10) | 263.19 (222.21, 311.72) | 0.155 | (12.08, 19.78) |
| | C21 (75 mg) Fasted (N = 9) | 1702.66 (1422.88, 2037.44) | | |

(N = number of subjects with non-missing values. A subject dropped out before receiving treatment under fasted condition).

The model is a mixed analysis of variance (ANOVA) model with a fixed term for sequence, period, treatment, and a random effect for subject within sequence.

Statistical analysis of the effect of food on C21 PK parameters (see Table 3 above) showed there was a decrease in $C_{max}$ when C21 was given with food. The geometric mean ratio for $C_{max}$ was 0.16, and the 90% confidence interval fell below 1 (100%), indicating that the $C_{max}$ difference was statistically significant. Administration of 75 mg C21 with food decreased $AUC_{(0-24)}$ and $AUC_{(0-inf)}$; the geometric mean ratios were both 0.45 and the 90% confidence intervals fell below 1 (100%) indicating the differences in AUC values were significant.

Example 2—Dissolution Studies (A)

50.7 mg of C21 sodium salt (Ardena, Riga, Latvia) was added to 900 mL of 0.09M carbonate buffer (pH 8.95) at a temperature of 37±3° C. with stirring. The compound dissolved instantly. After 15 minutes of stirring, 2M acetic acid solution was added dropwise to provide a pH of 4.52. Evolution $CO_2$ was noted. After stirring for 1 hour, the formation of small white particles was observed. After additional stirring for a further 1.5 hours, 1M NaOH was added to increase pH to 6.8. Stirring was continued for another 1.5 hours with no significant change in appearance (small white particles).

(B)

51.2 mg of C21 sodium salt was added to 900 mL of acetate buffer (pH 4.4) at the same temperature with stirring. The added compound formed a thin slurry which was floated on the surface top. After stirring for 1 hour, 1M NaOH solution was added dropwise to increase the pH to 7.2. The slurry became thinner and pieces became smaller and goo-like. Stirring was continued for another 1.5 hours with no significant change in appearance (small goo-like particles).

(C)

53.2 mg of C21 sodium salt was added to 900 mL 0.1M of HCl buffer (pH 1.0) at the same temperature with stirring. The added compound dissolved instantly. After 20 minutes of stirring, 1M NaOH solution was added dropwise to increase the pH to 4.5. After addition of the NaOH solution no precipitation was observed. After stirring for 2 hours formation solution still was clear.

(D)

51.0 mg of C21 sodium salt was added to 900 mL of 0.1M citrate buffer (pH 4.42) at the same temperature with stirring. The added compound formed a thin slurry. It seemed that nothing had dissolved. After stirring for 7 hours at the same temperature with no significant change in appearance. Analysis by UPLC showed no decomposition of C21 had occurred at the end of the experiment.

(E)

50.8 mg of C21 sodium salt was added to 900 mL of an acetate buffer (pH 4.49) at the same temperature. The added compound formed a thin slurry which floated on the surface. After stirring for 1 hour, a 1M NaOH solution was added dropwise to increase the pH to 6.8. The slurry became slightly thinner. Stirring was continued for another hour with no significant change in appearance. UPLC showed no decomposition of C21 had occurred at the end of the experiment.

Taken together, these results show that C21's Zwitterion that is formed at intermediated pHs is, unexpectedly, insoluble. This explains the food effect seen in Example 1 above.

Example 3—Dosage Form of the Invention

An excipient blend was prepared by weighing 21.4 g of colloidal silicon dioxide (Aerosil®; Evonik) into a weighing boat. 2033.8 g of mannitol (Pearlitol 50C, Roquette) was then weighed and approximately half of that amount was poured into to a 25 L V-shell of a V-blender (Multiblender, Pharmatech, UK). The weighed amount of colloidal silicon dioxide was then added to the V-shell, followed by the remaining mannitol. The resultant mixture was blended for 10 minutes at 30 rpm.

The excipient blend was then sieved through an 800 μm sieve, prior to blending for a further 20 minutes at 30 rpm.

Half of the resultant excipient blend was weighed and re-added to the V-shell. 528 g of C21 sodium salt (Ardena, Riga, Latvia) was then added to the V-shell. The remaining excipient blend was then added to the V-shell, followed by blending for 10 minutes at 30 rpm.

The resultant blend was then sieved through an 800 μm sieve, followed by blending for 20 minutes at 30 rpm.

After the blend was prepared, blend uniformity was determined by weighing about 270 mg of blend sample into a 100 mL volumetric flask, adding 40 mL of MilliQ water and 20 minutes of sonication, adding 40 mL of methanol and sonicating for a further 20 minutes. After equilibrating to room temperature, 1.0 mL of the sample solution was added to a 10 mL volumetric flask. This was followed by diluting to the desired volume with methanol and mixing.

The sample was filtered through a 0.45 μm PTFE membrane syringe filter, and the first 3 mL of the filtrate were discarded. The amount of C21 sodium salt was determined by UHPLC. The resulting solution should contain 0.1 mg/mL of C21 Na-salt (for 100% of the nominal sample concentration).

The results are shown in Table 4 below.

TABLE 4

| Sample | Assay (%, I.c.) |
|---|---|
| 1 | 100.3 |
| 2 | 102.1 |
| 3 | 104.1 |
| 4 | 100.9 |
| 5 | 98.7 |
| 6 | 99.3 |
| Mean | 100.9 |
| RSD | 1.9 |

After this, 26.1 g of magnesium stearate (Ligamed MF-2-V, Peter Greven, Germany) was sieved through an 800 μm sieve and added to the blend, following by final blending for 15 minutes at 15 rpm.

The final composition is as set out in Table 5 below.

TABLE 5

| Ingredient | Composition mg/capsule | % w/w |
|---|---|---|
| C21 sodium salt | 52.8 | 20.24 |
| mannitol (Pearlitol 50C) | 203.38 | 77.93 |
| colloidal silicon dioxide (Aerosil 200) | 2.14 | 0.82 |
| magnesium stearate (Ligamed MF-2-V) | 2.61 | 1.00 |

Approximately 6,700 capsules were encapsulated using an MG Compact (MG2, Bologna, Italy) with dosators Size 0, in which the following settings were applied chamber—11 mm; compression—0 mm; powder layer: 30.0 mm.

Weight sorting was done applying a 5% tolerance limit on the net fill weight of a capsule and was found to be 18.6%. After encapsulation the capsules were manually primary packaged in 100 mL high density polyethylene (HDPE) jars with child-resistant, tamper evident caps containing desiccant (56 capsules/jar). A total of 97 jars were produced and labelled for use in a clinical trial.

About 600 of these capsules (obtained according to the procedure described in Example 3 above) were coated using a pan coater (4M8TriX Pan Coater with a 2 L drum and a 0.7 mm diameter nozzle; ProCepT, Belgium) with an aqueous acrylic enteric coating system, which was applied as a 20% solution in water.

640 g of purified water was weighed into an 800 mL beaker and 160 g of pre-weighed Acryl-EZE® 93F19225 Clear (Colorcon) was then added gradually to the water with mechanical stirring for 20 minutes, placing the propeller stirrer in the centre and as close to the bottom of the vessel as possible, and forming a vigorous vortex to homogenize. The dispersion was passed through a 200 μm sieve prior to the coating process.

In order to promote good movement of the capsules within the pan coater and to reach the proper volume to be loaded into the drum, 560 dummy capsules (size 0) were also added, with a different capsules colour (dark green) and fill weight (410 mg/capsule of mannitol (Pearlitol 160C)), to allow for separation afterwards by weigh sorting and visual inspection.

A stepwise coating was performed with samples taken at predetermined times.

The coating process was performed by filling the drum with the capsules, setting the inlet temperature to 40° C.

Whilst the drum was turning, the capsules were heated to 30° C. before spraying the coating solution, at which point the final inlet temperature was set.

At the end of the coating process, the heating system was turned off and the capsules allowed to dry under slow tumbling.

The amount of sprayed solution was 740 g. The filling content per capsule of the composition is 260.93 mg per capsule. With an empty capsule weighing 96.1 mg and a total weight of 357 mg per filled capsule, the total weight per coated/filled capsule is 490.66 mg, which gives a coating amount per capsule of 133.66. This amounted to a weight of coating per capsule that was 139.08% of empty capsules and 37.44% of filled capsules.

The capsules were submitted to a *Ph. Eur.* (10th edition) standard (2.9.1 apparatus B; with disks) two-stage disintegration test subjecting coated capsules (n=6) to:
 (a) pH 1.2 (0.1N HCl in water, made by mixing 250 mL of 0.2M NaCl, 425 mL of 0.2M HCl and 325 mL of purified water); and
 (b) pH 6.8 using a phosphate buffer (made by mixing 250 mL of 0.2M potassium hydrogen phosphate, 112 mL of 0.2M NaOH and 638 mL of purified water).

The apparatus consisted of a basket-rack assembly, a device for raising and lowering the basket, a 1 L beaker and a thermostatic arrangement for heating the fluid at 37° C. (±2° C.). The basket-rack assembly was designed to contain 3 capsules in 3 different transparent cylinder tubes placed onto a stainless-steel screen, which allowed for entrance of the solution into the tubes.

For these experiments cylindric transparent plastic discs, with five holes, were placed on top of the floated capsules to keep them inside the tube during the test (without the discs the capsules would float on the surface of the media).

According to the *Ph. Eur.*, capsules with a gastro-resistant shell should survive for 2 hours in acid medium without showing signs of disintegration or rupture permitting the escape of the content.

After the 2 hours the basket-rack assembly was gently dried, and the coated capsules inspected visually in order to identify any sign of deformation or rupture.

Subsequently the basket was transferred into a phosphate buffer solution pH 6.8. According to the *Ph. Eur.* specification, all of the capsules should disintegrate within 60 minutes.

Visual inspection showed fully intact capsules in the acidic medium (a) and rapid capsule disintegration in the more basic medium (b) and, accordingly, that the capsules were successfully enterically-coated.

Example 4—Stability Study of the Dosage Form of the Invention

Enterically-coated capsules obtained using the method described in Example 3 above were tested in a study to evaluate the stability in a clinical representative packaging at ICH (International Council of Harmonisation) storage conditions (i) 25° C. and 60% RH (long term storage condition) and (ii) 40° C. and 75% RH (accelerated storage condition).

The final composition is as set out in Table 6 below.

TABLE 6

| Ingredients | Concentration (mg/capsule) 50 mg strength |
|---|---|
| C21 (free acid) | 50 |
| Mannitol (Pearlitol ® 50C) | 203.38 |

TABLE 6-continued

| Ingredients | Concentration (mg/capsule) 50 mg strength |
|---|---|
| Colloidal Silicium Dioxide (Aerosil ®) | 2.14 |
| Magnesium stearate (Ligamed ® MF-2-V) | 2.61 |
| Vcaps Plus, size 0, white opaque | 1 piece |
| Coating Layer (Acryl-EZE ®; % of empty capsule) | 139.08 |

The stability results under different storage conditions and time are presented in Tables 7 (assay and chromatographic purity) and 8 (disintegration) below. Water content was measured using the Karl Fischer titration method. Impurity 1 is previously known for C21, while impurities 2 and 3 are novel. LOR stands for limit of reporting (i.e. 0.10%, l.c.).

TABLE 7

| Condition | Time (months) | Water content (%, w/w) | C21 (%, l.c.) | Impurities (%, l.c.) | | | Sum (≤2) |
|---|---|---|---|---|---|---|---|
| | | | | 1 | 2 | 3 | |
| | Initial | — | 95.2 | 0.20 | 0.16 | <LOR | 0.36 |
| 25° C. and 60% RH | 3 | — | 97.8 | 0.22 | 0.15 | <LOR | 0.37 |
| | 4.5 | <0.5 | 98.8 | 0.24 | 0.15 | <LOR | 0.39 |
| | 6 | <0.5 | 100.7 | 0.24 | 0.15 | <LOR | 0.39 |
| 40° C. and 75% RH | 3 | — | 95.4 | 0.60 | 0.14 | <LOR | 0.75 |
| | 4.5 | <0.5 | 97.1 | 0.80 | 0.14 | <LOR | 0.94 |
| | 6 | <0.5 | 101.9 | 1.0 | 0.15 | <LOR | 1.2 |

TABLE 8

| Condition | Time (months) | Medium | Mean (min:s) | % RSD |
|---|---|---|---|---|
| | Initial | 0.1M HCl PH 1.2 | N/A | N/A |
| | | Phosphate buffer pH 6.8 | 33:55 | <0.1 |
| 25° C. and 60% RH | 3 | 0.1M HCl PH 1.2 | N/A | N/A |
| | | Phosphate buffer pH 6.8 | 28:57 | 6.9 |
| | 4.5 | 0.1M HCl PH 1.2 | N/A | N/A |
| | | Phosphate buffer pH 6.8 | 26:39 | 7.5 |
| | 6 | 0.1M HCl PH 1.2 | N/A | N/A |
| | | Phosphate buffer pH 6.8 | 31:48 | 8.8 |
| 40° C. and 75% RH | 3 | 0.1M HCl PH 1.2 | N/A | N/A |
| | | Phosphate buffer pH 6.8 | 25:24 | 7.8 |
| | 4.5 | 0.1M HCl PH 1.2 | N/A | N/A |
| | | Phosphate buffer pH 6.8 | 25:53 | 7.5 |
| | 6 | 0.1M HCl PH 1.2 | N/A | N/A |
| | | Phosphate buffer pH 6.8 | 27:57 | 6.2 |

All stability disintegration results were in line with the expectations, the enterically-coated capsules did not dissolve in acidic media and rapidly dissolved at pH 6.8. The assay was stable over the 6 months stability period at both storage conditions.

The invention claimed is:
1. A method of treatment of pulmonary fibrosis comprising:
 administering to the gastrointestinal tract of a patient in need of such treatment one or more compositions comprising N-butyloxycarbonyl-3-(4-imidazol-1-ylm- ethylphenyl)-5-iso-butylthiophene-2-sulfonamide, or a pharmaceutically-acceptable salt thereof, in which one or more compositions the N-butyloxycarbonyl-3-(4-imidazol-1-ylmethylphenyl)-5-iso-butylthiophene-2-sulfonamide or salt thereof is the sole active ingredient and is protected from being released from said one or more compositions within the stomach, wherein said administering provides a daily dose from said one or more compositions of N-butyloxycarbonyl-3-(4-imidazol-1-ylmethylphenyl)-5-iso-butylthiophene-2-sulfonamide, or said salt thereof, that is between about 10 mg and about 400 mg.

2. The method of treatment as claimed in claim 1, wherein the daily dose is between about 50 mg and about 200 mg.

3. The method of treatment as claimed in claim 1, wherein the N-butyloxycarbonyl-3-(4-imidazol-1-ylmethylphenyl)-5-iso-butylthiophene-2-sulfonamide or salt thereof is protected from being released from said one or more compositions within the stomach by the presence of an enteric substance.

4. The method of treatment as claimed in claim 3, wherein the enteric substance is polyvinyl acetate phthalate or a methacrylic acid copolymer.

5. The method of treatment as claimed in claim 3, wherein the enteric substance is provided as a coating on said one or more compositions, said one or more compositions comprising one or more capsules or one or more tablets.

6. The method of treatment as claimed in claim 1, wherein the N-butyloxycarbonyl-3-(4-imidazol-1-ylmethylphenyl)-5-iso-butyl-thiophene-2-sulfonamide or pharmaceutically-acceptable salt thereof is provided in the form of particles having a weight- and/or a volume-based mean diameter that is no more than about 50 μm.

7. The method of treatment as claimed in claim 1, wherein said one or more composition are essentially water-free.

8. The method of treatment as claimed in claim 1, wherein the pharmaceutically-acceptable salt of N-butyloxycarbonyl-3-(4-imidazol-1-ylmethyl-phenyl)-5-iso-butylthiophene-2-sulfonamide is a sodium salt.

9. The method of treatment as claimed in claim 1, wherein said N-butyloxycarbonyl-3-(4-imidazol-1-ylmethyl-phenyl)-5-iso-butylthiophene-2-sulfonamide or salt thereof is homogeneously dispersed along with a pharmaceutically acceptable carrier.

10. The method of treatment as claimed in claim 1, wherein the pulmonary fibrosis is idiopathic pulmonary fibrosis.

11. The method of treatment as claimed in claim 1, wherein the treatment includes prevention of morbidity and/or mortality from pulmonary fibrosis.

12. The method of treatment as claimed in claim 10, wherein the treatment includes prevention of morbidity and/or mortality from idiopathic pulmonary fibrosis.

13. The method of treatment as claimed in claim 1, wherein said administering is carried out perorally.

14. The method of treatment as claimed in claim 10, wherein said administering is carried out perorally.

15. The method of treatment as claimed in claim 3, wherein the enteric substance is selected from the group: cellulose acetate, cellulose acetate succinate, cellulose acetate phthalate, cellulose acetate tetrahydrophthalate, polyvinyl acetate phthalate, hydroxyethyl ethyl cellulose phthalate, a methacrylic acid copolymer, a polymethacrylic acid/acrylic acid copolymer, a styrol maleic acid copolymer, hydroxypropyl methyl cellulose phthalate, an acrylic resin, cellulose acetate trimellitate, hydroxypropyl methylcellulose trimellitate, shellac, hydroxyethyl ethyl cellulose phthalate, carboxymethylcellulose and hydroxypropyl methyl cellulose acetate succinate.

16. The method of treatment as claimed in claim 3, wherein the enteric substance is provided as a coating on said one or more compositions, said one or more compositions comprising one or more tablets.

* * * * *